US008003315B2

(12) United States Patent
Costa et al.

(10) Patent No.: US 8,003,315 B2
(45) Date of Patent: Aug. 23, 2011

(54) TAOJIKS AS MODIFIERS OF THE BETA-CATENIN PATHWAY AND METHODS OF USE

(75) Inventors: Michael A. Costa, San Francisco, CA (US); Steven Brian Gendreau, San Francisco, CA (US); Emery G. Dora, III, San Francisco, CA (US); Monique Nicoll, Pacifica, CA (US); Lenore Urbani, La Honda, CA (US); Jeffrey S. Larson, Burlingame, CA (US)

(73) Assignee: Exelixis, Inc., So. San Francisco, CA (US)

(*) Notice: Subject to any disclaimer, the term of this patent is extended or adjusted under 35 U.S.C. 154(b) by 0 days.

(21) Appl. No.: 10/317,835

(22) Filed: Dec. 12, 2002

(65) Prior Publication Data

US 2003/0157531 A1    Aug. 21, 2003

Related U.S. Application Data

(60) Provisional application No. 60/340,312, filed on Dec. 13, 2001.

(51) Int. Cl.
*C12Q 1/68* (2006.01)
*C12Q 1/48* (2006.01)
*G01N 33/53* (2006.01)

(52) U.S. Cl. .................. 435/6; 435/7.1; 435/15

(58) Field of Classification Search ...... 514/2; 530/300; 800/3
See application file for complete search history.

(56) References Cited

U.S. PATENT DOCUMENTS 6,165,461 A    12/2000  Cobb et al.
2003/0108937 A1*  6/2003  Williamson ............... 435/6

OTHER PUBLICATIONS

Houdebine (2000) Transgenic animal bioreactors. Transgenic Research. 9:305-320.*
Kolb (1999) Insertion of a foriegn gene into the beta-casein locus by Cre-mediated site-specific recombination. Gene 227:21-31.*
Vestraete (1999) Newer Throbolytic agents. Ann Acad. Med. Singapore; 28:424-33.*
Sadick MD (1999) Kinase receptor activation (KIRA): a rapid and accurate alternative to endpoint bioassays. Developments in Biological Standardization 97: 121-133 (abstract only).*
Hutchison,M., at al., "Homo sapiens thousand and one amino acid protein kinase (TA01), mRNA.", Genbank GI No. 4759207 [online], Nov. 1, 2000 [retrieved Dec. 12, 2002]. Retrieved from the Internet<URL:http:/www.ncbi.nim.nih.gov/entrez/query.fcgi?cmd=Retrieve&db=nudeotide&list_uids=4759207&dopt=GenBank>.
Strausberg,R., "*Homo sapiens*, Similar to thousand and one amino acid protein kinase, clone Image:3878048, mRNA.", Genbank GI No. 15929548 [online], Oct. 4, 2001 [retrieved Dec. 12, 2002]. Retrieved from the Internet:<URL:http:/www.ncbl.nlm,.nih.gov/entrez/query.fcgi?cmd=Retrieve&db=nucleotide&list_uids=15929548&dopt=GenBank>.
Moore, T.M., et al., "Homo sapiens prostate derived STE20-like kinase PSK (PSK), mRNA", Genbank GI No. 7706400 [online], Nov. 5, 2002 [retrieved Dec. 12, 2002]. Retrieved from the Internet:<URL:http://www.ncbi.nlm.nih.gov/entrez/query.fcgi?cmd=Retrieve&db=nucleotide&list_uids=7706400&dopt=GenBank>.
Tassi,E., et al., "Homo sapiens STE20-like kinase (JIK), mRNA.", Genbank GI No. 7705559 [online], Nov. 2, 2000 [retrieved Dec. 12, 2002]. Retrieved from the Internet<URL:http://www.ncbi.nlm.nih.gov/entrez/query.fcgi?cmd=Retrieve&db=nudeotide&list_uids=7705559&dopt=GenBank>.
NCBI Annotation Project., "Homo sapiens STE20-like kinase (JIK), mRNA.", Genbank GI No. 20552662 [online], May 13, 2002 [retrieved Dec. 12, 2002]. Retrieved from the Internet<URL:http://www.ncbi.nlm.nih.gov/entrez/query.fcgi?cmd=Retrieve&db=nudeotide&list_uids=20552662&dopt=GenBank>.
Strausberg,R., "Homo sapiens, STE20-like kinase, clone MGC:3364 Image:3630338.mRNA, complete cds.", Genbank GI No. 12803830 [online], Jul. 12, 2001 [retrieved on Dec. 12, 2002]. Retrieved from the Internet<URL:http://www.ncbi.nlm.nih.gov/entrex/query.fcgi?cmd=Retrieve&db=nucleotide&list_uids.12803830&dopt=GenBank>.
Carter,T.G., et al., "Homo sapiens STE20-like kinase (JIK), mRNA.", Genbank GI No. 19923463 [online], Apr. 4, 2002 [retrieved Dec. 12, 2002]. Retrieved from the Internet<URL:http://www.ncbi.nlm.nih.gov/entrez/query.fcgi?cmd=Retrieve&db=nucleotide&list_uids=19923463&dopt.GenBank>.
NCBI Annotation Project., "Homo sapiens STE20-like kinase (JIK), mRNA.", Genbank GI No. 15302531 [online], Feb. 7, 2002 [retrieved Dec. 12, 2002]. Retrieved from the Internet<URL:http://www.ncbi.nlm.nih.gov/entrez/query.lcgi?cmd=Retrieve&db=nucleotide&list_uids=15302531&dopt=GenBank>.
Nagase,T., el al., "Homo sapiens mRNA for KIAA1361 protein, partial cds.", Genbank GI No. 7243102 [online], Mar. 14, 2000 [retrieved Dec. 12, 2002]. Retrieved from the Internet:<URL:http:www.ncbi.nlm.nih.gov/entrez/query.fcgi?cmd=Retrieve&db=nucleotide&list_uids.7243102&dopt=GenBank>.
NCBI Annotation Project., "Homo sapiens KIAA1361 protein (KIAA1361), mRNA.", Genbank GI No. 18587661 [online], Feb. 7, 2002 [retrieved Dec. 12, 2002]. Retrieved from the Internet<URL:http://www.ncbi.nlm.nih.gov/entrez/query.fcgi?cmd=Retrieve&db=nucleoticle&list_uids=18587661&dopt=GenBank>.
NCBI Annotation Project., "Homo sapiens KIAA1361 protein (KIAA1361), mRNA.", Genbank GI No. 20559660 [online], May 13, 2002 [retrieved Dec. 12, 2002]. Retrieved from the Internet <URL:http:www.ncbi.nlm.nih.gov/entrez/query.fcgi?cmd=Retrieve&db=nucleotide&list_uids=20559660&dopt=GenBank>.

(Continued)

*Primary Examiner* — Anne-Marie Falk
(74) *Attorney, Agent, or Firm* — McDonnell Boehnen Hulbert & Berghoff LLP

(57) ABSTRACT

Human TAOJIK genes are identified as modulators of the beta-catenin pathway, and thus are therapeutic targets for disorders associated with defective beta-catenin function. Methods for identifying modulators of beta-catenin, comprising screening for agents that modulate the activity of TAOJIK are provided.

4 Claims, No Drawings

OTHER PUBLICATIONS

Yustein, J.T., et al., "*Homo sapiens* STE20-like kinase mRNA, partial cds" Genbank GI No. 11596143 [online], Dec. 7, 2000 [retrieved Dec. 12, 2002]. Retrieved from the Internet:<URL:http://www.ncbi.nlm.nih.gov/entrez/query.fcgi?cmd=Retrieve&db=nucleotide&list_uids=11596143&dopt=GenBank>.

Strausberg,R., "*Homo sapiens*, STE20-like kinase, clone MGC:3364 Image:3630338, mRNA, complete cds." Genbank GI No. 12803830 [online], Jul. 12, 2001 [retrieved Dec. 12, 2002]. Retrieved from the Internet: <URL:http://www.ncbi.nlm.nih.gov/entrez/query.fcgi?cmd=Retrieve&db=nucleotide&list_uids=12803830&dopt.GenBank>.

Hutchison.M., el al.,"thousand and one amino acid protein kinase [*Homo sapiens*]." Genbank GI No. 4759208 [online]. Nov. 1, 2000 [retrieved Dec. 12, 2002]. Retrieved from the Internet<URL:http://www.ncbi.nlm.nih.gov/entrez/query.fcgl?cmd=Retrieve&db=protein&list_uids.4759208&dopt=GenPept>.

Tassi,E., et al., "STE20-like kinase: STE2-like kinase [*Homo sapiens*].", Genbank GI No. 7705560 [online], Nov. 2, 2000 [retrieved Dec. 12, 2002]. Retrieved from the Internet<URL:http://www.ncbi.nlm.nlh.gov/entrez/query.fcgi?cmd?Retrieve&db=protein&list_uids.7705560&dopt=GenPept>.

Nagase,T., et al., "KIAA1361 protein [*Homo sapiens*]" Genbank GI No. 7243103 [online], Mar. 14, 2000 [retrieved Dec. 12, 2002]Retrieved from the Internet<URL:http://www.ncbi.nlm.nih.gov/entre/query.fcgi?cmd.Retrieve&db.protein&list_uids=7243103&dopt=GenPept>.

Williams Carol L et al.: "Reduced Expression of Wnt-1 and E-cadherin, and diminished beta-catenin stability in MCF-7 breast cancer cells that overexpress protein kinase C-alpha," International Journal of Oncology, vol. 19, No. 6, Dec. 2001, pp. 1227-1233, XP002394272.

Zhang Yi et al.: "Axin forms a complex with MEKK1 and activates c-Jun NH2, terminal kinase/stress-activated protein kinase through domains distinct from Wnt signaling," Journal of Biological Chemistry, vol. 274, No. 49, Dec. 3, 1999, pp. 35247-35254, XP002394562.

Sun T-Q et al.: "PAR-1 IA S Disheveled -Associated Kinase and a Positive Regulator of WNT Signaling," Nature Cell Biology, Macmillan Publishers, GB, vol. 3, No. 7, Jul. 2001, pp. 628-636, XP008004678.

Feraldo Marisa M. et al.: "Growth defect induced by perturbation of beta-inttegrin function in the mammary gland epithelium result from a lack of MAPK activation via the Shc and Akt Pathways," EMBO Reports, vol. 2, No. 5, May 2001, pp. 431-437, XP002394563.

Zhu B et al: "Inhibition of the Expression of Phosphodiesterase 5 by Antisense Inhibits the Growth of Human Colon Carcinoma (HT-29) Cells in Culture," FASEB Journal (Federation of American Societies for Experimental Biology), Bethesda, US, vol. 15, No. 5, Mar. 8, 2001, p. A924.

Tao Weikang et al: "Wrch-1, a novel member of the Rho gene family that is regulated by Wnt-1" Genes and Development, vol. 15, No. 14, Jul. 15, 2001, pp. 1796-1807.

Depraetere V: PAR-1 Helps WNT to Get Rid 1-31 of JNK: Nature Cell Biology, Macmillan Publishers, GB, vol. 3, Jul. 2001, pp. E158-E159.

Elena Tassi et al.: "Human JIK, a Novel Member of the STE20 Kinase Family That Inhibits JNK and Is Negatively Regulated by Epidermal Growth Factor," The Journal of Biological Chemistry, vol. 274, No. 47, Issue of Nov. 19, 1999, pp. 33287-33295.

\* cited by examiner

SEQUENCE LISTING

<160> NUMBER OF SEQ ID NOS: 18

<210> SEQ ID NO 1
<211> LENGTH: 4242
<212> TYPE: DNA

<213> ORGANISM: Homo sapiens

<400> SEQUENCE: 1

```
agaatttcaa atatcaggtt caggcccctg cgtgcaccag tatccggggt tcattccccg      60
ggcgttcaaa tatcggattc agtctccatc ccgttcagat attcggggtt cagaccccac     120
aatcagaaat ccggaattcg gcagctgtcg ccctcgacga gggggaggac tggaccgcga     180
ggtcagatta ggttgtcacc ccctcccctc caggggaggc ttcccgggcc cgcccctcag     240
gaagggcgaa agccgaggaa gaggtggcaa ggggaaaggt ctccttgccc ctctccctgc     300
ttggcagagc cgctggagga ccccaggcgg aagcggaggc gctggggcac catagtgacc     360
cctaccaggc caggccccac tctcagggcc ccaggggcc accatgccag ctggggccg      420
ggccgggagc ctgaaggacc cagatgtggc tgagctcttc ttcaaggatg acccagaaaa     480
gctcttctct gacctccggg aaattggcca tggcagcttt ggagccgtat actttgcccg     540
ggatgtccgg aatagtgagg tggtggccat caagaagatg tcctacagtg gaagcagtc     600
caatgagaaa tggcaagaca tcatcaagga ggtgcggttc ttacagaagc tccggcatcc     660
caacaccatt cagtaccggg gctgttacct gagggagcac acggcttggc tggtaatgga     720
gtattgcctg ggctcagctt ctgaccttct agaagtgcac aagaaacccc ttcaggaggt     780
agagatcgca gctgtgaccc acggggcgct caggcgcctg gcatatctgc actcccacaa     840
catgatccat agggatgtga aggctggaaa catcctgctg tcagagccag ggttagtgaa     900
gctaggggac tttggttctg cgtccatcat ggcacctgcc aactccttcg tgggcacccc     960
atactggatg gcacccgagg tgatcctggc catggatgag gggcagtacg atggcaaagt    1020
ggacgtctgg tccttgggga taacctgcat cgagctggct gaacgaaaac caccgctctt    1080
taacatgaat gcgatgagtg ccttatacca cattgcacag aacgaatccc ccgtgctcca    1140
gtcaggacac tggtctgagt acttccggaa ttttgtcgac tcctgtcttc agaaaatccc    1200
tcaagacaga ccaacctcag aggttctcct gaagcaccgc tttgtgctcc gggagcggcc    1260
acccacagtc atcatggacc tgatccagag gaccaaggat gccgtgcggg agctggacaa    1320
cctgcagtac cgcaagatga agaagatcct gttccaagag gcacccaacg ccctggtgc    1380
cgaggcccca gaggaggaag aggaggccga gccctacatg caccgggccg ggactctgac    1440
cagcctcgag agtagccact cagtgcccag catgtccatc agcgcctcca gccagagcag    1500
ctccgtcaac agcctagcag atgcctcaga caacgaggaa gaggaggagg aggaggagga    1560
agaggaggag gaggaagaag gccctgaagc ccgggagatg gccatgatgc aggaggggga    1620
gcacacagtc acctctcaca gctccattat ccaccggctg ccgggctctg acaacctata    1680
tgatgaccc taccagccag agataacccc cagccctctc cagccgcctg cagccccagc    1740
tcccacttcc accacctctt ctgcccgccg ccgggcctac tgccgtaacc gagaccactt    1800
tgccaccatc cgaaccgcct ccctggtcag ccgtcagatc caggagcatg agcaggactc    1860
tgcgctgcgg gagcagctga cggctataa cggatgcga cgacagcacc agaagcagct    1920
gctggccctg gagtcacggc tgaggggtga acggaggag cacagtgcac ggctgcagcg    1980
ggagcttgag gcgcagcggg ctggctttgg ggcagaggca gaaaagctgg cccggcggca    2040
ccaggccata ggtgagaagg aggcacgagc tgcccaggcc gaggagcgga gttccagca    2100
gcacatcctt gggcagcaga agaaggagct ggctgccctg ctggaggcac agaagcggac    2160
ctacaaactt cgcaaggaac agctgaagga ggagctccag agaaccccca gcactcccaa    2220
gcgggagaag gccgagtggc tgctgcggca gaaggagcag ctccagcagt gccaggcgga    2280
```

| | | | | | |
|---|---|---|---|---|---|
| ggaggaagca | gggctgctgc | ggcggcagcg | ccagtacttt | gagctgcagt | gtcgccagta | 2340 |
| caagcgcaag | atgttgctgg | ctcggcacag | cctggaccag | gacctgctgc | gggaggacct | 2400 |
| gaacaagaag | cagacccaga | aggacttgga | gtgtgcactg | ctgcttcggc | agcacgaggc | 2460 |
| cacgcgggag | ctggagctgc | ggcagctcca | ggccgtgcag | cgcacgcggg | ctgagctcac | 2520 |
| ccgcctgcag | caccagacgg | agctgggcaa | ccagctggag | tacaacaagc | ggcgtgagca | 2580 |
| agagttgcgg | cagaagcatg | cggcccaggt | tcgccagcag | cccaagagcc | tcaaatctaa | 2640 |
| ggagctgcag | atcaagaagc | agttccagga | gacgtgtaag | atccagactc | ggcagtacaa | 2700 |
| ggctctgcga | gcacacttgc | tggagaccac | gcccaaagct | cagcacaaga | gcctccttaa | 2760 |
| gcggctcaag | gaagagcaga | cccgcaagct | ggcgatcttg | gcggagcagt | atgaccagtc | 2820 |
| catctcagag | atgctcagct | cacaggcgct | gcggcttgat | gagacccagg | aggcagagtt | 2880 |
| ccaggccctt | cggcagcagc | ttcaacagga | gctggagctg | ctcaacgctt | accagagcaa | 2940 |
| gatcaagatc | cgcacagaga | gccagcacga | gaggagctg | cgggagctgg | agcagagggt | 3000 |
| cgcgctgcgg | cgggcactgc | tggagcagcg | ggtggaagag | gagctgctgg | ccctgcagac | 3060 |
| aggacgctcc | gagcgaatcc | gcagtctgct | tgagcggcag | gcccgtgaga | tcgaggcctt | 3120 |
| cgatgcggaa | agcatgaggc | tgggcttctc | cagcatggct | ctgggggca | tcccggctga | 3180 |
| agctgctgcc | cagggctatc | ctgctccacc | ccctgcccca | gctggccct | cccgtcccgt | 3240 |
| tccccgttct | ggggcacact | ggagccatgg | ccctcctcca | ccaggcatgc | cccctccagc | 3300 |
| ctggcgtcag | ccgtctctgc | tggctccccc | aggccccca | aactggctgg | gccccccac | 3360 |
| acaaagtggg | acaccccgtg | gcggagccct | gctgctgcta | agaaacagcc | cccagcccct | 3420 |
| gcggcgggca | gcctcggggg | gcagtggcag | tgagaatgtg | gccccccctg | ctgccgcggt | 3480 |
| gcccgggccc | ctgagccgca | gcaccagtgt | cgcttcccac | atcctcaatg | gttcttccca | 3540 |
| cttctattcc | tgaggtgcag | cggggaggag | cagatgagct | gggcagggca | ggggtggtg | 3600 |
| gagcctgacc | ctgagggca | ctgagctgga | ggccctgca | agggtagggg | acaagatgta | 3660 |
| ggctccagct | ccctcagac | ctcctcatct | catgagcttc | ttggggctgg | ccagtggccc | 3720 |
| agggccagct | tggcgataga | tgcctcaagg | ctgcctggga | gccccgcctc | cctaccatgg | 3780 |
| tgccaggggt | ctccctccgc | cacctaggaa | aggagggaga | tgtgcgtgtc | aaatattcat | 3840 |
| ctagtccct | gggggagggg | aagggtgggt | ctagacatac | tatattcaga | gaactatact | 3900 |
| accctcacag | tgaggccctc | agacctgcca | cagggcagag | caggtctggg | gcctgaggca | 3960 |
| gggagaatga | gaggccacct | tactggcagg | aaggatcagg | atgggtctt | ggggtcagga | 4020 |
| tgcctgggtc | tcttcccgta | actgtctgac | gtcctgtgcc | gtcttgtcct | ttatctttt | 4080 |
| tttttttttt | taattgggat | cagggctggg | gcggggaaac | aagggaagga | ccttggaagg | 4140 |
| ggctgctccc | aggcctgggg | ggcagtcgtg | ggagcccctc | tcagctgtgg | ggctggcaca | 4200 |
| gagccccagg | caagctttta | ataaactgtt | ggttattcta | ac | | 4242 |

<210> SEQ ID NO 2
<211> LENGTH: 3069
<212> TYPE: DNA
<213> ORGANISM: Homo sapiens

<400> SEQUENCE: 2

| | | | | | |
|---|---|---|---|---|---|
| gagaccggga | cgagaccggg | gctgtggtgc | ggagagaggc | tgagacggag | aagaggagag | 60 |
| gcagagaggg | cgcggggacc | gtcagcagca | ccttagctac | aatcgttcag | ctattctcgg | 120 |
| aagagagaag | ggagagggag | gaggccgggg | cgggagtggg | ggctgtcacc | ctcggacccc | 180 |

-continued

```
ggcgtgagag gggccgtgcg gccggacgtc ctcggggtgg gccccagtc ggtggccgaa      240
gacctacagc tcaggcccct gggtcccaaa tttccaggct ttgcccctcc tcctttctca      300
gatacccggg taacagtcct catagtccag atatccggga ctcgggtccc aacctctcta      360
aacctgggtc tctgtttcat agaatttcaa atatcaggtt caggcccctg cgtgcaccag      420
tatccggggt tcattccccg ggcgttcaaa tatcggattc agtctccatc ccgttcagat      480
attcggggtt cagaccccac aatcagaaat ccggaattcg gcagctgtcg ccctcgacga      540
gggggaggac tggaccgcga ggtcagatta ggttgtcacc ccctcccctc caggggaggc      600
ttcccgggcc cgcccctcag gaagggcgaa agccgaggaa gaggtggcaa ggggaaaggt      660
ctccttgccc ctctccctgc ttggcagagc cgctggagga cccaggcgg aagcggaggc       720
gctggggcac catagtgacc cctaccaggc caggccccac tctcagggcc ccaggggcc       780
accatgccag ctgggggccg ggccgggagc ctgaaggacc cagatgtggc tgagctcttc      840
ttcaaggatg acccagaaaa gctcttctct gacctccggg aaattggcca tggcagcttt      900
ggagccgtat actttgcccg ggatgtccgg aatagtgagg tggtggccat caagaagatg      960
tcctacagtg ggaagcagtc caatgagaaa tggcaagaca tcatcaagga ggtgcggttc     1020
ttacagaagc tccggcatcc caacaccatt cagtaccggg ctgttacct gagggagcac      1080
acggcttggc tggtaatgga gtattgcctg ggctcagctt ctgaccttct agaagtgcac     1140
aagaaacccc ttcaggaggt agagatcgca gctgtgaccc acggggcgct tcagggcctg     1200
gcatatctgc actcccacaa catgatccat agggatgtga aggctggaaa catcctgctg     1260
tcagagccag ggttagtgaa gctaggggac tttggttctg cgtccatcat ggcacctgcc     1320
aactccttcg tgggcacccc atactggatg cacccgagg tgatcctggc catggatgag      1380
gggcagtacg atggcaaagt ggacgtctgg tccttgggga taacctgcat cgagctggct     1440
gaacggaaac caccgctctt taacatgaat gcgatgagtg ccttatacca cattgcacag     1500
aacgaatccc ccgtgctcca gtcaggacac tggtctgagt acttccggaa ttttgtcgac     1560
tcctgtcttc agaaaatccc tcaagacaga ccaacctcag aggttctcct gaagcaccgc     1620
tttgtgctcc gggagcggcc acccacagtc atcatgacc tgatccagag gaccaaggat      1680
gccgtgcggg agctggacaa cctgcagtac cgcaagatga agaagatcct gttccaagag     1740
gcacccaacg ccctggtgc cgaggcccca gaggaggaag aggaggccga gccctacatg     1800
caccgggccg ggactctgac cagcctcgag agtagccact cagtgcccag catgtccatc     1860
agcgcctcca gccagagcag ctccgtcaac agcctagcag atgcctcaga caacgaggaa     1920
gaggaggagg aggaggagga gaggaggag gaggaagaag ccctgaagc ccgggagatg     1980
gccatgatgc aggaggggga gcacacagtc acctctcaca gctccattat ccaccggctg     2040
ccgggctctg acaacctata tgatgacccc taccagccag ataaccccc cagccctctc     2100
cagccgcctg cagcccccagc tcccacttcc accacctctt ctgcccgccg ccgggcctac     2160
tgccgtaacc gagaccactt tgccaccatc cgaaccgcct ccctggtcag ccgtcagatc     2220
caggagcatg agcaggactc tgcgctgcgg agcagctga gcggctataa gcggatgcga      2280
cgacagcacc agaagcagct gctggccctg gagtcacggc tgagggtga acgggaggag     2340
cacagtgcac ggctgcagcg ggagcttgag gcgcagcggg ctggctttgg ggcagaggca     2400
gaaaagctgg cccggcggca ccaggccata ggtgagaagg aggcacgagc tgcccaggcc     2460
gaggagcgga gttccagca gcacatcctt gggcagcaga agaaggagct ggctgccctg     2520
ctggaggcac agaagcggac ctacaaactt cgcaaggaac agctgaagga ggagctccag     2580
```

-continued

| | |
|---|---|
| gagaacccca gcactcccaa gcgggagaag gccgagtggc tgctgcggca aaggagcag | 2640 |
| ctccagcagt gccaggcgga ggaggaagca gggctgctgc ggcggcagcg ccagtacttt | 2700 |
| gagctgcagt gtcgccagta caagcgcaag atgttgctgg ctcggcacag cctggaccag | 2760 |
| gacctgctgc gggaggacct gaacaagaag cagacccaga aggacttgga gtgtgcactg | 2820 |
| ctgcttcggc agcacgaggc cacgcgggag ctggagctgc ggcagctcca ggccgtgcag | 2880 |
| cgcacgcggg ctgagctcac ccgcctgcag caccagacgg agctgggcaa ccagctggag | 2940 |
| tacaacaagc ggcgtgagca agagttgcgg cagaagcatg cggcccaggt tcgccagcag | 3000 |
| cccaagagcc tcaaaaaaaa gacaaacaca aataaaatat ctgagcggaa aaaaaaaaa | 3060 |
| aaaaaaaaa | 3069 |

<210> SEQ ID NO 3
<211> LENGTH: 3254
<212> TYPE: DNA
<213> ORGANISM: Homo sapiens

<400> SEQUENCE: 3

| | |
|---|---|
| ctggaggacc ccaggcggaa gcggaggcgc tggggcacca tagtgacccc taccaggcca | 60 |
| ggccccactc tcagggcccc caggggccac catgccagct gggggccggg ccgggagcct | 120 |
| gaaggaccca gatgtggctg agctcttctt caaggatgac ccagaaaagc tcttctctga | 180 |
| cctccgggaa attggccatg gcagctttgg agccgtatac tttgcccggg atgtccggaa | 240 |
| tagtgaggtg gtggccatca agaagatgtc ctacagtggg aagcagtcca atgagaaatg | 300 |
| gcaagacatc atcaaggagg tgcggttctt acagaagctc cggcatccca acaccattca | 360 |
| gtaccggggc tgttacctga gggagcacac ggcttggctg gtaatggagt attgcctggg | 420 |
| ctcagcttct gaccttctag aagtgcacaa gaaaccccct caggaggtag agatcgcagc | 480 |
| tgtgacccac ggggcgcttc agggcctggc atatctgcac tcccacaaca tgatccatag | 540 |
| ggatgtgaag gctggaaaca tcctgctgtc agagccaggg ttagtgaagc taggggactt | 600 |
| tggttctgcg tccatcatgg cacctgccaa ctccttcgtg gcacccccat actggatggc | 660 |
| acccgaggtg atcctggcca tggatgaggg gcagtacgat ggcaaagtgg acgtctggtc | 720 |
| cttggggata acctgcatcg agctggctga acggaaacca ccgctcttta acatgaatgc | 780 |
| gatgagtgcc ttataccaca ttgcacagaa cgaatccccc gtgctccagt caggacactg | 840 |
| gtctgagtac ttccggaatt ttgtcgactc ctgtcttcag aaaatcccct caagacagacc | 900 |
| aacctcagag gttctcctga agcaccgctt tgtgctccgg gagcggccac ccacagtcat | 960 |
| catggaccctg atccagagga ccaaggatgc cgtgcgggag ctggacaacc tgcagtaccg | 1020 |
| caagatgaag aagatcctgt tccaagaggc acccaacggc cctggtgccg aggccccaga | 1080 |
| ggaggaagag gaggccgagc cctacatgca ccgggccggg actctgacca gcctcgagag | 1140 |
| tagccactca gtgcccagca tgtccatcag cgcctccagc cagagcagct ccgtcaacag | 1200 |
| cctagcagat gcctcagaca cgaggaaga ggaggaggag gaggaggaag aggaggagga | 1260 |
| ggaagaaggc cctgaagccc gggagatggc catgatgcag gaggggagc acacagtcac | 1320 |
| ctctcacagc tccattatcc accggctgcc gggctctgac aacctatatg atgacccta | 1380 |
| ccagccagag ataaccccca gccctctcca gccgccctgca gccccagctc ccacttccac | 1440 |
| cacctcttcc gccccgccgc gggcctactg ccgtaaccga gaccactttg ccaccatccg | 1500 |
| aaccgcctcc ctggtcagcc gtcagatcca ggagcatgag caggactctg cgctgcggga | 1560 |
| gcagctgagc ggctataagc ggatgcgacg acagcaccag aagcagctgc tggccctgga | 1620 |

```
gtcacggctg aggggtgaac gggaggagca cagtgcacgg ctgcagcggg agcttgaggc    1680
gcagcgggct ggctttgggg cagaggcaga aaagctggcc cggcggcacc aggccatagg    1740
tgagaaggag gcacgagctg cccaggccga ggagcggaag ttccagcagc acatccttgg    1800
gcagcagaag aaggagctgg ctgccctgct ggaggcacag aagcggacct acaaacttcg    1860
caaggaacag ctgaaggagg agctccagga gaaccccagc actcccaagc gggagaaggc    1920
cgagtggctg ctgcggcaga aggagcagct ccagcagtgc caggcggagg aggaagcagg    1980
gctgctgcgg cggcagcgcc agtactttga gctgcagtgt cgccagtaca agcgcaagat    2040
gttgctggct cggcacagcc tggaccagga cctgctgcgg gaggacctga caagaagca     2100 gacccagaag gacttggagt gtgcactgct gcttcggcag cacgaggcca cgcgggagct    2160
ggagctgcgg cagctccagg ccgtgcacg cacgcgggct gagctcaccc gcctgcagca    2220
ccagacggag ctgggcaacc agctggagta caacaagcgg cgtgagcaag agttgcggca    2280
gaagcatgcg gcccaggttc gccagcagcc aagagcctc aaatctaagg agctgcagat    2340
caagaagcag ttccaggaga cgtgtaagat ccagactcgg cagtacaagg ctctgcgagc    2400
acacttgctg gagaccacgc ccaaagctca gcacaagagc ctccttaagc ggctcaagga    2460
agagcagacc cgcaagctgg cgatcttggc ggagcagtat gaccagtcca tctcagagat    2520
gctcagctca caggcgctgc ggcttgatga gacccaggag gcagagttcc aggcccttcg    2580
gcagcagctt caacaggagc tggagctgct caacgcttac cagagcaaga tcaagatccg    2640
cacagagagc cagcacgaga gggagctgcg ggagctggag cagagggtcg cgctgcggcg    2700
ggcactgctg gagcagcggg tggaagagga gctgctggcc ctgcagacag gacgctccga    2760
gcgaatccgc agtctgcttg agcggcaggc ccgtgagatc gaggccttcg atgcggaaag    2820
catgaggctg ggcttctcca gcatggctct ggggggcatc ccggctgaag ctgctgccca    2880
gggctatcct gctccacccc ctgccccagc ctggccctcc cgtccctgttc ccgttctgg    2940 ggcacactgg agccatggcc ctcctccacc aggcatgccc cctccagcct ggcgtcagcc    3000
gtctctgctg gctccccag ccccccaaa ctggctgggg cccccacac aaagtgggac     3060 acccegtggc ggagccctgc tgctgctaag aaacagcccc cagcccctgc ggcgggcagc    3120
ctcggggggc agtggcagtg agaatgtggg ccccctgct gccgcggtgc ccgggcccct    3180
gagccgcagc accagtgtcg cttcccacat cctcaatggt tcttcccact tctattcctg    3240
aggtgcagcg ggga                                                     3254
```

<210> SEQ ID NO 4
<211> LENGTH: 4971
<212> TYPE: DNA
<213> ORGANISM: Homo sapiens

<400> SEQUENCE: 4

```
aattcggcac gagctgagac ggagaagagg agaggcagag agggcgcggg gaccgtcagc      60
agcaccttag ctacaatcgt tcagctattc tcggaagaga gaagggagag ggaggaggcc     120
ggggcgggag tggggctgt caccctcgga ccccggcgtg agaggggccg tgcggccgga      180
cgtcctcggg gtgggccccc agtcggtggc cgaagaccta cagctcaggc ccctgggtcc     240
caaatttcca ggctttgccc ctcctccttt ctcagatacc cggtaacag tcctcatagt      300 ccagatatcc gggactcggg tcccaacctc tctaaacctg gtctctgtt tcatagattt      360 tcaaatatca ggttcaggcc cctgcgtgca ccagtatccg ggttcattc cccgggcgtt     420 tcaaatatcg gattcagtct ccatcccgtt cagatattcg gggttcagac cccacaatca    480
```

-continued

| | |
|---|---|
| gaaatccgga attcggcagc tgtcgccctc gacgagggggg aggactggac cgcgaggtca | 540 |
| gattaggttg tcaccccctc ccctccaggg gaggcttccc gggcccgccc ctcaggaagg | 600 |
| gcgaaagccg aggaagaggt ggcaaggga aggtctcct tgcccctctc cctgcttggc | 660 |
| agagccgctg gaggacccca ggcggaagcg gaggcgctgg ggcaccatag tgacccctac | 720 |
| caggccaggc cccactctca gggcccccag gggccaccat gccagctggg ggccgggccg | 780 |
| ggagcctgaa ggacccagat gtggctgagc tcttcttcaa ggatgaccca gaaaagctct | 840 |
| tctctgacct ccgggaaatt ggccatggca gctttggagc cgtatacttt gcccgggatg | 900 |
| tccggaatag tgaggtggtg gccatcaaga agatgtccta cagtgggaag cagtccaatg | 960 |
| agaaatggca agacatcatc aaggaggtgc ggttcttaca gaagctccgg catcccaaca | 1020 |
| ccattcagta ccggggctgt tacctgaggg agcacacggc ttggctggta atggagtatt | 1080 |
| gcctgggctc agcttctgac cttctagaag tgcacaagaa accccttcag gaggtagaga | 1140 |
| tcgcagctgt gacccacggg gcgcttcagg gcctggcata tctgcactcc cacaacatga | 1200 |
| tccatagga tgtgaaggct ggaaacatcc tgctgtcaga gccagggtta gtgaagctag | 1260 |
| gggactttgg ttctgcgtcc atcatggcac ctgccaactc cttcgtgggc accccatact | 1320 |
| ggatggcacc cgaggtgatc ctggccatgg atgagggca gtacgatggc aaagtggacg | 1380 |
| tctggtcctt ggggataacc tgcatcgagc tggctgaacg gaaaccaccg ctctttaaca | 1440 |
| tgaatgcgat gagtgcctta taccacattg cacagaacga atccccgtg ctccagtcag | 1500 |
| gacactggtc tgagtacttc cggaattttg tcgactcctg tcttcagaaa atccctcaag | 1560 |
| acagaccaac ctcagaggtt ctcctgaagc accgctttgt gctccgggag cggccaccca | 1620 |
| cagtcatcat ggacctgatc cagaggacca aggatgccgt gcgggagctg acaacctgc | 1680 |
| agtaccgcaa gatgaagaag atcctgttcc aagaggcacc caacggccct ggtgccgagg | 1740 |
| ccccagagga ggaagaggag gccgagcccc acatgcaccg gccgggact ctgaccagcc | 1800 |
| tcgagagtag ccactcagtg cccagcatgt ccatcagcgc ctccagccag agcagctccg | 1860 |
| tcaacagcct agcagatgcc tcagacaacg aggaagagga ggaggaggag gaggaagagg | 1920 |
| aggaggagga agaaggccct gaagcccggg agatggccat gatgcaggag ggggagcaca | 1980 |
| cagtcacctc tcacagctcc attatccacc ggctgccggg ctctgacaac ctatatgatg | 2040 |
| accccctacca gccagagata accccagcc ctctccagcc gcctgcagcc ccagctccca | 2100 |
| cttccaccac ctcttccgcc cgccgccggg cctactgccg taaccgagac cactttgcca | 2160 |
| ccatccgaac cgcctccctg gtcagccgtc agatccagga gcatgagcag gactctgcgc | 2220 |
| tgcgggagca gctgagcggc tataagcgga tgcgacgaca gcaccagaag cagctgctgg | 2280 |
| ccctggagtc acggctgagg ggtgaacggg aggagcacag tgcacggctg cagcgggagc | 2340 |
| ttgaggcgca gcgggctggc tttgggggcag aggcagaaaa gctggccgg cggcaccagg | 2400 |
| ccataggtga aaggaggca cgagctgccc aggccgagga gcggaagttc cagcagcaca | 2460 |
| tccttgggca gcagaagaag gagctggctg ccctgctgga ggcacagaag cggacctaca | 2520 |
| aacttcgcaa ggaacagctg aaggaggagc tccaggagaa ccccagcact cccaagcggg | 2580 |
| agaaggccga gtggctgctg cggcagaagg agcagctcca gcagtgccag gcggaggagg | 2640 |
| aagcagggct gctgcggcgg cagcgccagt actttgagct gcagtgtcgc cagtacaagc | 2700 |
| gcaagatgtt gctggctcgg cacagcctgg accaggacct gctgcgggag gacctgaaca | 2760 |
| agaagcagac ccagaaggac ttggagtgtg cactgctgct tcggcagcac gaggccacgc | 2820 |
| gggagctgga gctgcggcag ctccaggccg tgcagcgcac gcgggctgag ctcacccgcc | 2880 |

```
tgcagcacca acggagctg ggcaaccagc tggagtacaa caagcggcgt gagcaagagt    2940
tgcggcagaa gcatgcggcc caggttcgcc agcagcccaa gagcctcaaa gtacgtgcag    3000
gccagcgccc cccggggcctt ccactcccca ttcctggggc tctgggccca cccaacacag   3060
gcacccctat agaacagcag ccctgctcac ctggccagga ggcagtcctg gaccaaagaa    3120
tgcttggcga ggaggaggaa gcagttggag agagaaggat tctgggaaag gaaggggcca    3180
ctttggagcc caagcagcag aggattctgg gggaagaatc aggagcccct agtcccagtc    3240
cacaaaaaca tgggagcctg gttgatgagg aagtttgggg tctgcctgag gagatagagg    3300
agcttagggt gccctcccctt gtaccccagg agaggagcat tgttggccag gaggaggctg    3360
ggacgtggag cttgtggggg aaggaggatg agagtcttct ggatgaggag tttgagcttg    3420
gctgggtcca gggcccagca ctgactcccg tccctgagga ggaggaagaa gaggaagagg    3480
gggctccgat tgggacccct agggatcctg gagatggttg tccttccccc gacatccctc    3540
ctgaaccccc tccaacacac ctgaggcccct gccctgccag ccagctccct ggactcctgt    3600
cccatggcct cctggccggc ctctccttttg cagtggggtc ctcctctggc ctcctgcccc    3660
tcctgctgct gctgctgctt ccattgctgg cagcccaggg tgggggtggc ctgcaggcag   3720
cgctgctggc ccttgaggtg gggctggtgg gtctggggggc ctcctacctg ctcctttgta   3780
cagccctgca cctgccctcc agtcttttcc tactcctggc ccagggtacc gcactggggg    3840
ccgtcctggg cctgagctgg cgccgaggcc tcatgggtgt tcccctgggc cttggagctg    3900
cctggctctt agcttggcca ggcctagctc tacctctggt ggctatggca gcggggggca   3960
gatgggtgcg gcagcagggc cccccgggtgc gccggggcat atctcgactc tggttgcggg   4020
ttctgctgcg cctgtcaccc atggccttcc gggcccctgca gggctgtggg gctgtggggg   4080
accggggtct gtttgcactg taccccaaaa ccaacaagga tggcttccgc agccgcctgc    4140
ccgtccctgg gccccggcgg cgtaatcccc gcaccaccca acacccatta gctctgttgg    4200
caagggtctg ggtcctgtgc aagggctgga actggcgtct ggcacgggcc agccagggtt    4260
tagcatccca cttgccccccg tgggccatcc acacactggc cagctggggc ctgcttcggg   4320
gtgaacggcc cacccgaatc ccccggctac taccacgcag ccagcgccag ctagggcccc    4380
ctgcctccca ccagccactg ccagggactc tagccgggcg gaggtcacgc acccgccagt    4440
cccgggccct gcccccctgg aggtagctga ctccagccct tccagcccaa atctagagca    4500
ttgagcactt tatctcccac gactcagtga agtttctcca gtccctagtc ctctcttttc    4560
acccaccttc ctcagtttgc tcacttaccc caggcccagc ccttcggacc tctagacagg    4620
cagcctcctc agctgtggag tccagcagtc actctgtgtt ctcctggcgc tcctccccta    4680
agttattgct gttcgcccgc tgtgtgtgct catcctcacc ctcattgact caggcctggg    4740
gccaggggtg gtggagggtg ggaagagtca tgttttttttt ctcctctttg attttgtttt    4800
tctgtctccc ttccaacctg tccccttccc ccaccaaaa aagaaaaag acaaacacaa     4860
ataaaatatc tgagcggaac tgtgaaaaaa aaaaaaaaa aaaaaaaaa aaaaaaaaa      4920
aaaaaaaaa aaaaaaaaa aaaaaaaaa aaaaaaaaa aaaaaaaaa a               4971
```

<210> SEQ ID NO 5
<211> LENGTH: 2958
<212> TYPE: DNA
<213> ORGANISM: Homo sapiens

<400> SEQUENCE: 5

```
acggccatta ccaatcgcga aaccaaagga ctgaagttat aaaagagaaa agagaagttt      60
```

```
gctgctaaaa tgaatctgag caatatggaa tattttgtgc cacacacaaa aaggtactga    120
agatttaccc cccaaaaaaa attgtcaatg agaaataaag ctaactgata tcaaaaagca    180
gagcctgctg tactggccat catgcgtaaa ggggtgctga aggacccaga gattgccgat    240
ctattctaca aagatgatcc tgaggaactt tttattggtt tgcatgaaat tggacatgga    300
agttttggag cagtttattt tgctacaaat gctcacacca gtgaggtggt ggcaattaag    360
aagatgtcct atagtgggaa gcagacccat gagaaatggc aagatattct taaggaagtt    420 aaattttac  gacaattgaa gcatcctaat actattgagt acaaaggctg ttacttgaaa    480
gaacacactg cttggttggt gatggaatat tgcttaggct cagcctctga tttattagaa    540
gttcataaaa aaccacttca ggaagtggag atcgctgcca ttactcatgg agccttgcat    600
ggactagcct acctacattc tcatgcattg attcataggg atattaaagc aggaaatatt    660
cttctaacag agccaggtca ggtaaaacta gctgattttg gatctgcttc aatggcttct    720
cctgccaact ccttcgtggg cacaccttac tggatggctc cagaagtgat cttagctatg    780
gatgaaggac agtatgatgg gaaagttgat atttggtcac ttggcatcac ttgtattgaa    840
ttggcggaac ggaagccgcc ccttttcaac atgaatgcaa tgagtgcctt atatcacatt    900
gcccagaatg actccccaac gttacagtct aatgaatgga cagactcctt taggagattt    960
gttgattact gcttgcagaa aatacctcag gaaaggccaa catcagcaga actattaagg   1020
catgactttg ttcgacgaga ccggccacta cgtgtcctca ttgacctcat acagaggaca   1080
aaagatgcgg ttcgtgagct agataaccta cagtaccgaa aaatgaaaaa aatactttc    1140 caagagacac ggaatggacc cttgaatgag tcacaggagg atgaggaaga cagtgaacat   1200
ggaaccagcc tgaacaggga atggacagc  ctgggcagca accattccat tccaagcatg   1260
tccgtaacat ggaaccagcc tgaacaggga atggacagc  ctgggcagca accattccat   1320
tccaagcatg tccgtgtcat gatgcacgat gacgaaagca caatcaattc cagctcctcc   1380
gtcgtgcata agaaagatca tgtattcata agggatgagg cgggccacgg cgatcccagg   1440
cctgagccgc ggcctaccca gtcagttcag agccaggccc tccactaccg gaacagagag   1500
cgctttgcca cgatcaaatc agcatctttg gttacgcgac agatccatga gcatgagcag   1560
gagaacgagt tgcgggaaca gatgtcaggt tataagcgga tgcggcgcca gcaccagaag   1620
cagctgatcg ccctgagaa  caagctgaag gctgagatgg acgagcaccg cctcaagcta   1680
cagaaggagg tggagacgca tgccaacaac tcgtccatcg agctggagaa gctggccaag   1740
aagcaagtgc tatcataga  aaaggaggca aaggtagctg cagcagatga gaagaagttc   1800
cagcaacaga tcttggccca gcagaagaaa gatttgacaa cttttcttaga aagtcagaag   1860 aagcagtata gatttgtaa  ggaaaaaata aagaggaaa  tgaatgagga ccatagcaca   1920
cccaagaaag agaagcaaga gcggatctcc aaacataaag agaacttgca gcacacacag   1980
gctgaagagg aagcccacct tctcactcaa cagagactgt actacgacaa aaattgtcgt   2040
ttcttcaagc ggaaaataat gatcaagcgg cacgaggtgg agcagcagaa cattcgggag   2100
gaactaaata aaaagaggac ccagaaggag atggagcatg ccatgctaat ccggcacgac   2160
gagtccaccc gagagctaga gtacaggcag ctgcacacgt acagaagct  acgcatggat   2220 ctgatccgtt tacagcacca gacggaactg gaaaaccagc tggagtacaa taagaggcga   2280
gaaagagaac tgcacagaaa gcatgtcatg gaacttcggc aacagccaaa aaacttaaag   2340
gccatggaaa tgcaaattaa aaaacagttt caggacactt gcaaagtaca gaccaaacag   2400
tataaagcac tcaagaatca ccagttggaa gttactccaa agaatgagca caaaacaatc   2460
```

-continued

```
ttaaagacac tgaaagatga gcagacaaga aaacttgcca ttttggcaga gcagtatgaa      2520
cagagtataa atgaaatgat ggcctctcaa gcgttacggc tagatgaggc tcaagaagca      2580
gaatgccagg ccttgaggct acagctccag caggaaatgg agctgctcaa cgcctaccag      2640
agcaaaatca agatgcaaac agaggcacaa catgaacgtg agctccagaa gctagagcag      2700
agagtgtctc tgcgcagagc acaccttgag cagaagattg aagaggagct ggctgccctt      2760
cagaaggaac gcagcgagag aataaagaac ctattggaaa ggcaagagcg agagattgaa      2820
acttttgaca tggagagcct cagaatggga tttgggaatt tggttacatt agattttcct      2880
aaggaggact acagatgaga ttaaattttt ttccatttac aaaaaaaaaa aaaaaaaaa      2940 aaaaaaaaaa aaaaaaaa                                                    2958

<210> SEQ ID NO 6
<211> LENGTH: 2897
<212> TYPE: DNA
<213> ORGANISM: Homo sapiens

<400> SEQUENCE: 6
caaaggactg aagttataaa agagaaaaga gaagtttgct gctaaaatga atctgagcaa        60
tatggaatat tttgtgccac acacaaaaag gtactgaaga tttaccccc aaaaaaaatt       120 gtcaatgaga aataaagcta actgatatca aaaagcagag cctgctctac tggccatcat       180
gcgtaaaggg gtgctgaagg acccagagat tgccgatcta ttctacaaag atgatcctga       240
ggaacttttt attggtttgc atgaaattgg acatggaagt tttggagcag tttattttgc       300
tacaaatgct cacaccagtg aggtggtggc aattaagaag atgtcctata gtgggaagca       360
gacccatgag aaatggcaag atattcttaa ggaagttaaa ttttacgac aattgaagca       420 tcctaatact attgagtaca aaggctgtta cttgaaagaa cacactgctt ggttggtgat       480
ggaatattgc ttaggctcag cctctgattt attagaagtt cataaaaaac cacttcagga       540
agtggagatc gctgccatta ctcatggagc cttgcatgga ctagcctacc tacattctca       600
tgcattgatt cataggggata ttaaagcagg aaatattctt ctaacagagc caggtcaggt       660
aaaactagct gattttggat ctgcttcaat ggcttctcct gccaactcct tcgtgggcac       720
accttactgg atggctccag aggtgatctt agctatggat gaaggacagt atgatgggaa       780
agttgatatt tggtcacttg gcatcacttg tattgaattg gcggaacgga agccgccct       840 tttcaacatg aatgcaatga gtgccttata tcacattgcc cagaatgact ccccaacgtt       900
acagtctaat gaatggacag actcctttag gagatttgtt gattactgct tgcagaaaat       960
acctcaggaa aggccaacat cagcagaact attaaggcat gactttgttc gacgagaccg      1020
gccactacgt gtcctcattg acctcataca gaggacaaaa gatgcagttc gtgagctaga      1080
taacctacag taccgaaaaa tgaaaaaaat actttccaa gagacacgga atggacccctt      1140 gaatgagtca caggaggatg aggaagacag tgaacatgga accagcctga cagggaat      1200 ggacagcctg ggcagcaacc attccattcc aagcatgtcc gtgagcacag gcagccagag      1260
cagcagtgtg aacagcatgc aggaagtcat ggacgagagc agttccgaac ttgtcatgat      1320
gcacgatgac gaaagcacaa tcaattccag ctcctccgtc gtgcataaga aagatcatgt      1380
attcataagg gatgaggcgg ccacggcga tcccaggcct gagccgcggc ctacccagtc      1440
agttcagagc caggccctcc actaccggaa cagagagcgc tttgccacga tcaaatcagc      1500
atctttggtt acacgacaga tccatgagca tgagcaggag aacgagttgc gggaacagat      1560
gtcaggttat aagcggatgc ggcgccagca ccagaagcag ctgatcgccc tggagaacaa      1620
```

| | |
|---|---|
| gctgaaggct gagatggacg agcaccgcct caagctacag aaggaggtgg agacgcatgc | 1680 |
| caacaactcg tccatcgagc tggagaagct ggccaagaag caagtggcta tcatagaaaa | 1740 |
| ggaggcaaag gtagctgcag cagatgagaa gaagttccag caacagatct tggcccagca | 1800 |
| gaagaaagat ttgacaactt tcttagaaag tcagaagaag cagtataaga tttgtaagga | 1860 |
| aaaaataaaa gaggaaatga atgaggacca tagcacaccc aagaaagaga agcaagagcg | 1920 |
| gatctccaaa cataaagaga acttgcagca cacacaggct gaagaggaag cccaccttct | 1980 |
| cactcaacag agactgtact acgacaaaaa ttgtcgtttc ttcaagcgga aaataatgat | 2040 |
| caagcggcac gaggtggagc agcagaacat tcgggaggaa ctaaataaaa agaggaccca | 2100 |
| gaaggagatg gagcatgcca tgctaatccg gcacgacgag tccacccgag agctagagta | 2160 |
| caggcagctg cacacgttac agaagctacg catggatctg atccgtttac agcaccagac | 2220 |
| ggaactggaa aaccagctgg agtacaataa gaggcgagaa agagaactgc acagaaagca | 2280 |
| tgtcatggaa cttcggcaac agccaaaaaa cttaaaggcc atggaaatgc aaattaaaaa | 2340 |
| acagtttcag gacacttgca aagtacagac caaacagtat aaagcactca agaatcacca | 2400 |
| gttggaagtt actccaaaga atgagcacaa aacaatctta aagacactga agatgagcga | 2460 |
| gacaagaaaa cttgccattt tggcagagca gtatgaacag agtataaatg aaatgatggc | 2520 |
| ctctcaagcg ttacggctag atgaggctca agaagcagaa tgccaggcct tgaggctaca | 2580 |
| gctccagcag gaaatggagc tgctcaacgc ctaccagagc aaaatcaaga tgcaaacaga | 2640 |
| ggcacaacat gaacgtgagc tccagaagct agagcagaga gtgtctctgc gcagagcaca | 2700 |
| ccttgagcag aagattgaag aggagctggc tgcccttcag aaggaacgca gcgagagaat | 2760 |
| aaagaaccta ttggaaaggc aagagcgaga gattgaaact tttgacatgg agagcctcag | 2820 |
| aatgggattt gggaatttgg ttacattaga ttttcctaag gaggactaca gatgagatta | 2880 |
| aatttttttgc catttac | 2897 |

<210> SEQ ID NO 7
<211> LENGTH: 3148
<212> TYPE: DNA
<213> ORGANISM: Homo sapiens

<400> SEQUENCE: 7

| | |
|---|---|
| ggcacgagggg tggcgccggg cggcggggtc ctgcgtggag agtgggacgc aacgccgaga | 60 |
| ccgcgagcag aggctgcgca cagccggatc cggcactcag cgaccggacc caaggatccg | 120 |
| ccggggaaca agccacagga gagcgactca ggaacaagtg tgggagagga agcggcggcg | 180 |
| gcggcgccgg gcccgggggt ggtgacagca ggtctgaggt tgcatcataa atacaaagga | 240 |
| ctgaagttat aaaagagaaa agagaagttt gctgctaaaa tgaatctgag caatatggaa | 300 |
| tattttgtgc cacacacaaa aaggtactga agatttaccc cccaaaaaaa attgtcaatg | 360 |
| agaaataaag ctaactgata tcaaaaagca gagcctgctc tactggccat catgcgtaaa | 420 |
| ggggtgctga aggacccaga gattgccgat ctattctaca aagatgatcc tgaggaactt | 480 |
| tttattggtt tgcatgaaat tggacatgga agttttggag cagtttatttt tgctacaaat | 540 |
| gctcacacca gtgaggtggt ggcaattaag aagatgtcct atagtgggaa gcagacccat | 600 |
| gagaaatggc aagatattct taaggaagtt aaatttttac gacaattgaa gcatcctaat | 660 |
| actattgagt acaaaggctg ttacttgaaa gaacacactg cttggttggt gatggaatat | 720 |
| tgcttaggct cagcctctga tttattagaa gttcataaaa aaccacttca ggaagtggag | 780 |
| atcgctgcca ttactcatgg agccttgcat ggactagcct acctacattc tcatgcattg | 840 |

-continued

```
attcataggg atattaaagc aggaaatatt cttctaacag agccaggtca ggtaaaacta      900
gctgattttg gatctgcttc aatggcttct cctgccaact ccttcgtggg cacaccttac      960
tggatggctc cagaggtgat cttagctatg gatgaaggac agtatgatgg gaaagttgat     1020
atttggtcac ttggcatcac ttgtattgaa ttggcggaac ggaagccgcc ccttttcaac     1080
atgaatgcaa tgagtgcctt atatcacatt gcccagaatg actccccaac gttacagtct     1140
aatgaatgga cagactcctt taggagattt gttgattact gcttgcagaa atacctcag      1200 gaaaggccaa catcagcaga actattaagg catgactttg ttcgacgaga ccggccacta     1260
cgtgtcctca ttgacctcat acagaggaca aagatgcag ttcgtgagct agataaccta      1320
cagtaccgaa aaatgaaaaa aatacttttc caagagacac ggaatggacc cttgaatgag     1380
tcacaggagg atgaggaaga cagtgaacat ggaaccagcc tgaacaggga atggacagc      1440 ctgggcagca accattccat tccaagcatg tccgtgagca caggcagcca gagcagcagt     1500
gtgaacagca tgcaggaagt catggacgag agcagttccg aacttgtcat gatgcacgat     1560
gacgaaagca caatcaattc cagctcctcc gtcgtgcata agaaagatca tgtattcata     1620
agggatgagg cgggccacgg cgatcccagg cctgagccgc ggcctaccca gtcagttcag     1680
agccaggccc tccactaccg gaacagagag cgctttgcca cgatcaaatc agcatctttg     1740
gttacacgac agatccatga gcatgagcag gagaacgagt tgcggaaaca gatgtcaggt     1800
tataagcgga tgcggcgcca gcaccagaag cagctgatcg ccctggagaa caagctgaag     1860
gctgagatgg acgagcaccg cctcaagcta cagaaggagg tggagacgca tgccaacaac     1920
tcgtccatcg agctggagaa gctggccaag aagcaagtgg ctatcataga aaaggaggca     1980
aaggtagctg cagcagatga gaagaagttc cagcaacaga tcttggccca gcagaagaaa     2040
gatttgacaa ctttcttaga aagtcagaag aagcagtata gatttgtaa ggaaaaaata      2100 aaagaggaaa tgaatgagga ccatagcaca cccaagaaag agaagcaaga gcggatctcc     2160
aaacataaag agaacttgca gcacacacag gctgaagagg aagcccacct tctcactcaa     2220
cagagactgt actacgacaa aaattgtcgt ttcttcaagc ggaaaataat gatcaagcgg     2280
cacgaggtgg agcagcagaa cattcgggag gaactaaata aaaagaggac ccagaaggag     2340
atggagcatg ccatgctaat ccggcacgac gagtccaccc gagagctaga gtacaggcag     2400
ctgcacacgt tacagaagct acgcatggat ctgatccgtt tacagcacca gacggaactg     2460
gaaaaccagc tggagtacaa taagaggcga gaaagagaac tgcacagaaa gcatgtcatg     2520
gaacttcggc aacagccaaa aaacttaaag gccatgaaaa tgcaaattaa aaaacagttt     2580
caggacactt gcaaagtaca gaccaaacag tataaagcac tcaagaatca ccagttggaa     2640
gttactccaa agaatgagca caaaacaatc ttaaagacac tgaaagatga gcagacaaga     2700
aaacttgcca ttttggcaga gcagtatgaa cagagtataa atgaaatgat ggcctctcaa     2760
gcgttacggc tagatgaggc tcaagaagca gaatgccagg ccttgaggct acagctccag     2820
caggaaatgg agctgctcaa cgcctaccag agcaaaatca agatgcaaac agaggcacaa     2880
catgaacgtg agctccagaa gctagagcag agagtgtctc tgcgcagagc acaccttgag     2940
cagaagattg aagaggagct ggctgccctt cagaaggaac gcagcgagag aataaagaac     3000
ctattggaaa ggcaagagcg agagattgaa acttttgaca tggagagcct cagaatggga     3060
tttgggaatt tggttacatt agattttcct aaggaggact acagatgaga ttaaattttt     3120 tgccattac aaaaaaaaaa aaaaaaaa                                          3148
```

<210> SEQ ID NO 8

<211> LENGTH: 4188
<212> TYPE: DNA
<213> ORGANISM: Homo sapiens

<400> SEQUENCE: 8

| | | | | | |
|---|---|---|---|---|---|
| gccggggaac | aagccacagg | agagcgactc | aggaacaagt | gtgggagagg | aagcggcggc | 60 |
| ggcggcgccg | ggcccggggg | tggtgacagc | aggtctgagg | ttgcatcata | aatacaaagg | 120 |
| actgaagtta | taaagagaa | aagagaagtt | tgctgctaaa | atgaatctga | gcaatatgga | 180 |
| atattttgtg | ccacacacaa | aaaggtactg | aagatttacc | ccccaaaaaa | aattgtcaat | 240 |
| gagaaataaa | gctaactgat | atcaaaaagc | agagcctgct | ctactggcca | tcatgcgtaa | 300 |
| aggggtgctg | aaggacccag | agattgccga | tctattctac | aaagatgatc | ctgaggaact | 360 |
| ttttattggt | ttgcatgaaa | ttggacatgg | aagttttgga | gcagtttatt | ttgctacaaa | 420 |
| tgctcacacc | aatgaggtgg | tggcaattaa | gaagatgtcc | tatagtggga | agcagaccca | 480 |
| tgagaaatgg | caagatattc | ttaaggaagt | taaattttta | cgacaattga | agcatcctaa | 540 |
| tactattgag | tacaaaggct | gttacttgaa | agaacacact | gcttggttgg | tgatggaata | 600 |
| ttgcttaggc | tcagcctctg | atttattaga | agttcataaa | aaaccacttc | aggaagtgga | 660 |
| gatcgctgcc | attactcatg | gagccttgca | tggactagcc | tacctacatt | ctcatgcatt | 720 |
| gattcatagg | gatattaaag | caggaaatat | tcttctaaca | gagccaggtc | aggtaaaact | 780 |
| agctgatttt | ggatctgctt | caatggcttc | tcctgccaac | tccttcgtgg | gcacaccta | 840 |
| ctggatggct | ccagaggtga | tcttagctat | ggatgaagga | cagtatgatg | ggaaagttga | 900 |
| tatttggtca | cttggcatca | cttgtattga | attggcggaa | cggaagccgc | ccttttcaa | 960 |
| catgaatgca | atgagtgcct | tatatcacat | tgcccagaat | gactcccaa | cgttacagtc | 1020 |
| taatgaatgg | acagactcct | ttaggagatt | tgttgattac | tgcttgcaga | aaatacctca | 1080 |
| ggaaaggcca | acatcagcag | aactattaag | gcatgacttt | gttcgacgag | accggccact | 1140 |
| acgtgtcctc | attgacctca | tacagaggac | aaaagatgca | gttcgtgagc | tagataacct | 1200 |
| acagtaccga | aaaatgaaaa | aaatactttt | ccaagagaca | cggaatggac | ccttgaatga | 1260 |
| gtcacaggag | gatgaggaag | acagtgaaca | tggaaccagc | tgaacaggg | aaatggacag | 1320 |
| cctgggcagc | aaccattcca | ttccaagcat | gtccgtgagc | acaggcagcc | agagcagcag | 1380 |
| tgtgaacagc | atgcaggaag | tcatggacga | gagcagttcc | gaacttgtca | tgatgcacga | 1440 |
| tgacgaaagc | acaatcaatt | ccagctcctc | cgtcgtgcat | aagaaagatc | atgtattcat | 1500 |
| aagggatgag | gcgggccacg | gcgatcccag | gcctgagccg | cggcctaccc | agtcagttca | 1560 |
| gagccaggcc | ctccactacc | ggaacagaga | gcgctttgcc | acgatcaaat | cagcatcttt | 1620 |
| ggttacacga | cagatccatg | agcatgagca | ggagaacgag | ttgcgggaac | agatgtcagg | 1680 |
| ttataagcgg | atgcggcgcc | agcaccagaa | gcagctgatc | gccctggaga | caagctgaa | 1740 |
| ggctgagatg | gacgagcacc | gcctcaagct | acagaaggag | gtggagacgc | atgccaacaa | 1800 |
| ctcgtccatc | gagctggaga | agctggccaa | gaagcaagtg | gctatcatag | aaaaggaggc | 1860 |
| aaaggtagct | gcagcagatg | agaagaagtt | ccagcaacag | atcttggccc | agcagaagaa | 1920 |
| agatttgaca | actttcttag | aaagtcagaa | gaagcagtat | aagatttgta | aggaaaaaat | 1980 |
| aaaagaggaa | atgaatgagg | accatagcac | acccaagaaa | gagaagcaag | agcggatctc | 2040 |
| caaacataaa | gagaacttgc | agcacacaca | ggctgaagag | gaagcccacc | ttctcactca | 2100 |
| acagagactg | tactacgaca | aaaattgtcg | tttcttcaag | cggaaaataa | tgatcaagcg | 2160 |
| gcacgaggtg | gagcagcaga | acattcggga | ggaactaaat | aaaagagga | cccagaagga | 2220 |

-continued

| | | | |
|---|---|---|---|
| gatggagcat gccatgctaa tccggcacga cgagtccacc cgagagctag agtacaggca | | | 2280 |
| gctgcacacg ttacagaagc tacgcatgga tctgatccgt ttacagcacc agacggaact | | | 2340 |
| ggaaaaccag ctggagtaca ataagaggcg agaaagagaa ctgcacagaa agcatgtcat | | | 2400 |
| ggaacttcgg caacagccaa aaaacttaaa ggccatggaa atgcaaatta aaaaacagtt | | | 2460 |
| tcaggacact tgcaaagtac agaccaaaca gtataaagca ctcaagaatc accagttgga | | | 2520 |
| agttactcca aagaatgagc acaaaacaat cttaaagaca ctgaaagatg agcagacaag | | | 2580 |
| aaaacttgcc attttggcag agcagtatga acagagtata aatgaaatga tggcctctca | | | 2640 |
| agcgttacgg ctagatgagg ctcaagaagc agaatgccag gccttgaggc tacagctcca | | | 2700 |
| gcaggaaatg gagctgctca acgcctacca gagcaaaatc aagatgcaaa cagaggcaca | | | 2760 |
| acatgaacgt gagctccaga agctagcaga gagagtgtct ctgcgcagag cacaccttga | | | 2820 |
| gcagaagatt gaagaggagc tggctgccct tcagaaggaa cgcagcgaga gaataaagaa | | | 2880 |
| cctattggaa aggcaagagc gagagattga aacttttgac atggagagcc tcagaatggg | | | 2940 |
| atttgggaat ttggttacat tagatttttcc taaggaggac tacagatgag attaaatttt | | | 3000 |
| ttgccattta caaaaaaaaa aaaaaaaaga aaacagaaaa aaattcagac cctgcaaaac | | | 3060 |
| cacattcccc attttaacgg gcgttgctct cactctctct ctctcttact cttactgaca | | | 3120 |
| tcgtgtcgga ctagtgcctg tttattctta ctccatcagg ggccccccttc ctcccccgt | | | 3180 |
| gtcaactttc agtgctggcc aaaacctggc cgtctcttct attcacagta cacgtcacag | | | 3240 |
| tattgatgtg attcaaaatg tttcagtgaa aactttggag acagttttaa caaaaccaat | | | 3300 |
| aaaccaacaa caaaaaaagt ggatgtatat tgctttaagc aatcactcat taccaccaat | | | 3360 |
| ctgtgaaagt aaagcaaaaa ataataataa taaatgccaa gggggagaga gacacaatat | | | 3420 |
| ccgcagcctt acaccttaac tagctgctgc attatttat tttattttat ttttttggta | | | 3480 |
| tttattcatc aggaataaaa aaaacaaagt tttattaaag attgaaaatt tgatacattt | | | 3540 |
| tacagaaact aattgtgatg tacatatcag tggtgacata ttattacttt tttggggacg | | | 3600 |
| ggggtgggtg gggtgaagag atcttgtgat tttagactgc tgcagagtta acttgtctca | | | 3660 |
| gcatatctga tgtatcataa tcatttctgc tgtgcagagg agggatacac ttaggggctc | | | 3720 |
| acagatccca gtagcacaat tgggcttttgg caaatgggta ttttgtgtat agaggaattt | | | 3780 |
| aaggagaggt attacttatt ttcatattgt attttaactg tttctcggat caaattttt | | | 3840 |
| aacttcttct tcgtgttctt ccccacctcc ttccttttcc agttcagtat ttggagttca | | | 3900 |
| acactgtctc tcaatcagat catctggatc tttttctta tctcccttcc ccttcctaag | | | 3960 |
| tcccatttct tggtcataaa tattgcatta ttcacacttt caaactgtgt attttcttac | | | 4020 |
| aataaaaaat gatgaaaaaa aaaaaggctt tacttctttt gcatgcactt taaaaacaaa | | | 4080 |
| acaaaacatt tttcaggttc caaggaagag catgataact gtcagagctt ttaattatat | | | 4140 |
| ttgtaaataa aagtgttcat cacaaaaaaa aaaaaaaaa aaaaaaaa | | | 4188 |

<210> SEQ ID NO 9
<211> LENGTH: 2807
<212> TYPE: DNA
<213> ORGANISM: Homo sapiens

<400> SEQUENCE: 9

| | | | |
|---|---|---|---|
| gtactgaaga tttaccccccc aaaaaaaatt gtcaatgaga aataaagcta actgatatca | | | 60 |
| aaaagcagag cctgctctac tggccatcat gcgtaaaggg gtgctgaagg acccagagat | | | 120 |
| tgccgatcta ttctacaaag atgatcctga ggaacttttt attggtttgc atgaaattgg | | | 180 |

```
acatggaagt tttggagcag tttattttgc tacaaatgct cacaccagtg aggtggtggc      240
aattaagaag atgtcctata gtgggaagca gacccatgag aaatggcaag atattcttaa      300
ggaagttaaa tttttacgac aattgaagca tcctaatact attgagtaca aaggctgtta      360
cttgaaagaa cacactgctt ggttggtgat ggaatattgc ttaggctcag cctctgattt      420
attagaagtt cataaaaaac cacttcagga agtggagatc gctgccatta ctcatggagc      480
cttgcatgga ctagcctacc tacattctca tgcattgatt cataggggata ttaaagcagg     540 aaatattctt ctaacagagc caggtcaggt aaaactagct gattttggat ctgcttcaat      600
ggcttctcct gccaactcct tcgtgggcac accttactgg atggctccag aggtgatctt      660
agctatggat gaaggacagt atgatgggaa agttgatatt tggtcacttg gcatcacttg      720
tattgaattg gcggaacgga agccgccccct tttcaacatg aatgcaatga gtgccttata    780
tcacattgcc cagaatgact ccccaacgtt acagtctaat gaatggacag actcctttag      840
gagatttgtt gattactgct tgcagaaaat acctcaggaa aggccaacat cagcagaact      900
attaaggcat gactttgttc gacgagaccg gccactacgt gtcctcattg acctcataca      960
gaggacaaaa gatgcagttc gtgagctaga taacctacag taccgaaaaa tgaaaaaaat     1020
acttttccaa gagacacgga atggaccctt gaatgagtca caggaggatg aggaagacag     1080
tgaacatgga accagcctga cagggaaat ggacagcctg gcagcaacc attccattcc       1140 aagcatgtcc gtgagcacag gcagccagag cagcagtgtg aacagcatgc aggaagtcat     1200
ggacgagagc agttccgaac ttgtcatgat gcacgatgac gaaagcacaa tcaattccag     1260
ctcctccgtc gtgcataaga aagatcatgt attcataagg gatgaggcgg ccacggcga      1320 tcccaggcct gagccgcggc ctacccagtc agttcagagc caggccctcc actaccggaa     1380
cagagagcgc tttgccacga tcaaatcagc atctttggtt acacgacaga tccatgagca     1440
tgagcaggag aacagttgc gggaacagat gtcaggttat aagcggatgc ggcgccagca     1500
ccagaagcag ctgatcgccc tggagaacaa gctgaaggct gagatggacg agcaccgcct     1560
caagctacag aaggaggtgg agacgcatgc caacaactcg tccatcgagc tggagaagct     1620
ggccaagaag caagtggcta tcatagaaaa ggaggcaaag gtagctgcag cagatgagaa     1680
gaagttccag caacagatct tggcccagca agaaaagat ttgacaactt tcttagaaag     1740
tcagaagaag cagtataaga tttgtaagga aaaaataaaa gaggaaatga atgaggacca     1800
tagcacaccc aagaaagaga agcaagagcg gatctccaaa cataaagaga acttgcagca     1860
cacacaggct gaagaggaag cccaccttct cactcaacag agactgtact acgacaaaaa     1920
ttgtcgtttc ttcaagcgga aaataatgat caagcggcac gaggtggagc agcagaacat     1980
tcgggaggaa ctaaataaaa agaggaccca agggagatg gagcatgcca tgctaatccg      2040
gcacgacgag tccacccgag agctagagta caggcagctg cacacgttac agaagctacg     2100
catggatctg atccgtttac agcaccagac ggaactggaa aaccagctgg agtacaataa     2160
gaggcgagaa agagaactgc acagaaagca tgtcatggaa cttcggcaac agccaaaaaa     2220
cttaaaggcc atggaaatgc aaattaaaaa acagtttcag gacacttgca aagtacagac     2280
caaacagtat aaagcactca agaatcacca gttggaagtt actccaaaga tgagcacaa     2340 aacaatctta aagacactga agatgagca gacaagaaaa cttgccattt tggcagagca     2400
gtatgaacag agtataaatg aaatgatggc ctctcaagcg ttacggctag atgaggctca     2460
agaagcagaa tgccaggcct tgaggctaca gctccagcag gaaatggagc tgctcaacgc     2520
ctaccagagc aaaatcaaga tgcaaacaga ggcacaacat gaacgtgagc tccagaagct     2580
```

-continued

| | |
|---|---|
| agagcagaga gtgtctctgc gcagagcaca ccttgagcag aagattgaag aggagctggc | 2640 |
| tgcccttcag aaggaacgca gcgagagaat aaagaaccta ttggaaaggc aagagcgaga | 2700 |
| gattgaaact tttgacatgg agagcctcag aatgggattt gggaatttgg ttacattaga | 2760 |
| ttttcctaag gaggactaca gatgagatta aatttttttgc catttac | 2807 |

<210> SEQ ID NO 10
<211> LENGTH: 4620
<212> TYPE: DNA
<213> ORGANISM: Homo sapiens

<400> SEQUENCE: 10

| | |
|---|---|
| gagccgtgat tgtgccacta cactccagcc ctgacctctt acaccgaagc agtcctcata | 60 |
| cgtcagcctc ccaaagtgct gggattacag atgaaccaag gatcgggata gcagtataaa | 120 |
| attagaatca agacagctga ctgctcagca ggatgccatc aactaacaga gcaggcagcc | 180 |
| tgaaggaccc tgaaattgca gagctcttct tcaaagaaga tccagagaag ctcttcacag | 240 |
| atctcagaga aattggccat ggaagctttg gagcagtgta ttttgcacga gatgtgcgta | 300 |
| ccaatgaagt ggtggccatc aagaaaatgt cttatagtgg aaagcagtct actgagaaat | 360 |
| ggcaggatat tattaaggaa gtcaagtttc tacaaagaat aaaacatccc aacagtatag | 420 |
| aatacaaagg ctgttattta cgtgaacaca cagcatggct tgtaatggaa tattgtttag | 480 |
| gatctgcttc ggatttacta gaagttcaca aaaagccatt acaagaagtg gaaatagcag | 540 |
| caattacaca tggtgctctt cagggattag cctacttaca ttctcatact atgattcata | 600 |
| gagatatcaa agcaggaaat atccttctga cagaaccagg ccaggtgaaa cttgctgact | 660 |
| ttggctctgc ttccatggca tcacctgcca attcctttgt gggaacgccg tattggatgg | 720 |
| ccccagaagt aattttagcc atggatgaag acaatatga tggcaaagta gatgtgtggt | 780 |
| ctcttggaat aacatgtatt gaactagcgg aaaggaagcc tccttttattt aatatgaatg | 840 |
| caatgagtgc cttatatcac atagcccaaa atgaatcccc tacactacag tctaatgaat | 900 |
| ggtctgatta ttttcgcaac tttgtagatt cttgcctcca gaaaatccct caagatcgac | 960 |
| ctacatcaga ggaactttta aagcacatat ttgttcttcg ggagcgccct gaaaccgtgt | 1020 |
| taatagatct cattcagagg acaaaggatg cagtaagaga gctggacaat ctgcagtatc | 1080 |
| gaaagatgaa gaaactcctt ttccaggagg cacataatgg accagcagta gaagcacagg | 1140 |
| aagaagaaga ggaacaagat catggtgttg gccggacagg aacagttaat agtgttggaa | 1200 |
| gtaatcaatc cattcccagc atgtccatca gtgccagcag ccaaagcagt agtgttaaca | 1260 |
| gtcttccaga tgtctcagat gacaagagtg agctagacat gatggaggga gaccacacag | 1320 |
| tgatgtctaa cagttctgtt atccatttaa accagagga agaaaattac agagaagagg | 1380 |
| gagatcctag aacaagagca tcagatccac aatctccacc ccaagtatct cgtcacaaat | 1440 |
| cacactatcg taatcgagaa cactttgcta ctatacggac agcatcactg gttacgaggc | 1500 |
| aaatgcaaga acatgagcag gactctgagc ttagagaaca aatgtctggc tataagcgaa | 1560 |
| tgaggcgaca acatcaaaag caactgatga ctctggaaaa caagctaaag ctgagatggg | 1620 |
| atgaacatcg cctcagatta gacaaagatc ttgaaactca gcgtaacaat tttgctgcag | 1680 |
| aaatggagaa acttatcaag aaacaccagg ctgctatgga aaagaggct aaagtgatgt | 1740 |
| ccaatgaaga gaaaaatttt cagcaacata ttcaggccca acagaagaaa gaactgaata | 1800 |
| gttttctcga gtcccagaaa agagagtata acttcgaaaa agagcagctt aaagaggagc | 1860 |
| taaatgaaaa ccagagtacc cccaaaaaag aaaaacagga gtggctttca aagcagaagg | 1920 |

```
agaatataca gcatttccaa gcagaagaag aagctaacct tcttcgacgt caaagacaat    1980
acctagagct ggaatgccgt cgcttcaaga gaagaatgtt acttgggcgt cataacttag    2040
agcaggacct tgtcagggag gagttaaaca aaagacagac tcagaaggac ttagagcatg    2100
ccatgctact ccgacagcat gaatctatgc aagaactgga gttccgccac ctcaacacaa    2160
ttcagaagat gcgctgtgag ttgatcagat tacagcatca aactgagctc actaaccagc    2220
tggaatataa taagcgaaga gaacgagaac taagacgaaa gcatgtcatg gaagttcgac    2280
aacagcctaa gagtttgaag tctaaagaac tccaaataaa aaagcagttt caggatacct    2340
gcaaaatcca aaccagacag tacaaagcat taagaaatca cctgctggag actacaccaa    2400
agagtgagca caaagctgtt ctgaaacggc tcaaggagga acagacccgg aaattagcta    2460
tcttggctga gcagtatgat cacagcatta atgaaatgct ctccacacaa gccctgcgtt    2520
tggatgaagc acaggaagca gagtgccagg ttttgaagat gcagctgcag caggaactgg    2580
agctgttgaa tgcgtatcag agcaaaatca agatgcaagc tgaggcacaa catgatcgag    2640
agcttcgcga gcttgaacag agggtctccc tccggagggc actcttagaa caaaagattg    2700
aagaagagat gttggctttg cagaatgagc gcacagaacg aatacgaagc ctgttggaac    2760
gtcaagccag agagattgaa gcttttgact ctgaaagcat gagactaggt tttagtaata    2820
tggtcctttc taatctctcc cctgaggcat tcagccacag ctacccggga gcttctggtt    2880
ggtcacacaa ccctactggg ggtccaggac ctcactgggg tcatcccatg ggtggcccac    2940
cacaagcttg gggccatcca atgcaaggtg accccagcc atgggtcac ccttcagggc    3000 caatgcaagg ggtacctcga ggtagcagta tgggagtccg caatagcccc caggctctga    3060
ggcggacagc ttctggggga cggacagagc agggcatgag cagaagcacg agtgtcactt    3120
cacaaatatc caatgggtca cacatgtctt atacataact taataattga gagtggcaat    3180
tccgctggag ctgtctgcca aaagaaactg cctacagaca tcatcacagc agcctcctca    3240
cttgggtact acagtgtgga agctgagtgc atatggtata ttttattcat ttttgtaaag    3300
cgttctgttt tgtgtttact aattgggatg tcatagtact tggctgccgg gtttgtttgt    3360
ttttggggaa attttgaaaa gtggagttga tattaaaaat aaatgtgtat gtgtgtacat    3420
atatatacac acacatacac atatattatg catgtggtga aaagaattgg ctagataggg    3480 gattttctg aacactgcaa aaatagaacg tagcaaaatg gcttcagtta tcacttttgg    3540
gtgtctgtat cctaagaagt ttctgaaaag atctaaagcc tttttatccc atatcccaaa    3600
ttcttatgag ccactcacag caggcagcat atgttgaaat aagttattac tggtacacac    3660
ctgcattgcc tcaccagtgt atttatttgt tattaaattg atctgacttc tcagcctcat    3720
ttggactaaa aaagaaagc agaaatccat gaacacattg cttctcggcc ttttggctaa    3780
gatcaagtgt agaaatccat gaacactaaa ggacttcatt gattttttca gagagtagaa    3840
aacaacttag tttttctttt ttcctgaatg cgtcataggc ttgtgagtga tttttgtcca    3900
ttcaattgtg ccttctttgt attatgataa gatgggggta cttaaggaga tcacaagttg    3960
tgtgaggatt gcattaacaa acctatgagc cttcaatggg gaagaccaga agggtgagag    4020
gggccctgaa agttcatatg gtgggtatgt cccgcagcag agtgaggaga tgaagcttac    4080
gtgtcctgac gttttgttgc ttatactgtg atatctcatc ctagctaagc tctataatgc    4140
ccgagacccc aaacagtact tttactttgt ttgtacaaaa acaaagacat atagccaata    4200
caaatcaaat gccggaggtg tttgatgcca tatttgcaaa ttgccatcta ttgaaattct    4260
cgtcacacta catagacata attgttatct ccttttggct tatgtgattt tctgtttaca    4320
```

```
agtagaatag ccaattattt aaatgtttag ttgccacagt gaaccaggag tcactgagcc    4380
aatgacttta ccagctgctg actaatcttc atcaccactg tagattttgc tgcatgtgca    4440
ggtcctctat ttttaattgc tgttttcgtt gctgcagtac tttacaaact tctagttcgt    4500
tgagacttag tgaccatttg gcatcaagtt aacatcacac aataggaaac accacttcca    4560
caagtctcaa gcctcagtgc taaagtacta ctgaaaagga actaggaagt ttggccaatt    4620
```

<210> SEQ ID NO 11
<211> LENGTH: 4536
<212> TYPE: DNA
<213> ORGANISM: Homo sapiens
<220> FEATURE:
<221> NAME/KEY: misc_feature
<222> LOCATION: (1)..(4536)
<223> OTHER INFORMATION: "n" is A, C, G, or T

<400> SEQUENCE: 11

```
tacagatgaa ccaaggatcg ggatagcagt ataaaattag aatcaagaca gctgactgct      60
cagcaggatg ccatcaacta acagagcagg cagcctgaag gaccctgaaa ttgcagagct     120
cttcttcaaa gaagatccag agaagctctt cacagatctc agagaaattg gccatggaag     180
ctttggagca gtgtattttg cacgagatgt gcgtaccaat gaagtggtgg ccatcaagaa     240
aatgtcttat agtggaaagc agtctactga gaaatggcag gatattatta aggaagtcaa     300
gtttctacaa agaataaaac atcccnaaca gtatagaata caaaggctgt tatttacgtg     360
aacacacagc atggcttgta atggaatatt gtttaggatc tgcttcggat ttactagaag     420
ttcacaaaaa gccattacaa gaagtggaaa tagcagcaat tacacatggt gctcttcagg     480
gattagccta cttacattct catactatga ttcatagaga tatcaaagca ggaaatatcc     540
ttctgacaga accaggccag gtgaaacttg ctgactttgg ctctgcttcc atggcatcac     600
ctgccaattc ctttgtggga acgccgtatt ggatggcccc agaagtaatt ttagccatgg     660
atgaaggaca atatgatggc aaagtagatg tgtggtctct tggaataaca tgtattgaac     720
tagcggaaag gaagcctcct ttatttaata tgaatgcaat gagtgcctta tatcacatag     780
cccaaaatga atcccctaca ctacagtcta atgaatggtc tgattatttt cgcaactttg     840
tagattcttg cctccagaaa atccctcaag atcgacctac atcagaggaa cttttaaagc     900
acatatttgt tcttcgggag cgccctgaaa ccgtgttaat agatctcatt cagaggacaa     960
aggatgcagt aagagagctg gacaatctgc agtatcgaaa gatgaagaaa ctcctttttcc    1020 aggaggcaca taatggacca gcagtagaag cacaggaaga agaagaggaa caagatcatg    1080
gtgttggccg gacaggaaca gttaatagtg ttggaagtaa tcaatccatt cccagcatgt    1140
ccatcagtgc cagcagccaa agcagtagtg ttaacagtct tccagatgtc tcagatgaca    1200
agagtgagct agacatgatg gagggagacc acacagtgat gtctaacagt tctgttatcc    1260
atttaaaacc agaggaagaa aattacagag aagagggaga tcctagaaca agagcatcag    1320
atccacaatc tccaccccaa gtatctcgtc acaaatcaca ctatcgtaat cgagaacact    1380
ttgctactat acggacagca tcactggtta cgaggcaaat gcaagaacat gagcaggact    1440
ctgagcttag agaacaaatg tctggctata gcgaatgag gcgacaacat caaaagcaac    1500
tgatgactct ggaaaacaag ctaaaggctg agatggatga acatcgcctc agattagaca    1560
aagatcttga aactcagcgt aacaattttg ctgcagaaat ggagaaactt atcaagaaac    1620
accaggctgc tatggagaaa gaggctaaag tgatgtccaa tgaagagaaa aaatttcagc    1680
aacatattca ggcccaacag aagaaagaac tgaatagttt tctcgagtcc cagaaaagag    1740
```

```
agtataaact tcgaaaagag cagcttaaag aggagctaaa tgaaaaccag agtacccccca   1800 aaaaagaaaa acaggagtgg ctttcaaagc agaaggagaa tatacagcat ttccaagcag   1860
aagaagaagc taaccttctt cgacgtcaaa gacaatacct agagctggaa tgccgtcgct   1920
tcaagagaag aatgttactt gggcgtcata acttagagca ggaccttgtc agggaggagt   1980
taaacaaaag acagactcag aaggacttag agcatgccat gctactccga cagcatgaat   2040
ctatgcaaga actggagttc cgccacctca acacaattca aagatgcgc tgtgagttga    2100 tcagattaca gcatcaaact gagctcacta accagctgga atataataag cgaagagaac   2160
gagaactaag acgaaagcat gtcatggaag ttcgacaaca gcctaagagt ttgaagtcta   2220
aagaactcca ataaaaaag cagtttcagg atacctgcaa aatccaaacc agacagtaca    2280
aagcattaag aaatcacctg ctggagacta caccaaagag tgagcacaaa gctgttctga   2340
aacggctcaa ggaggaacag acccggaaat tagctatctt ggctgagcag tatgatcaca   2400
gcattaatga aatgctctcc acacaagccc tgcgtttgga tgaagcacag gaagcagagt   2460
gccaggtttt gaagatgcag ctgcagcagg aactggagct gttgaatgcg tatcagagca   2520
aaatcaagat gcaagctgag gcacaacatg atcgagagct tcgcgagctt gaacagaggg   2580
tctccctccg gagggcactc ttagaacaaa agattgaaga agagatgttg gctttgcaga   2640
atgagcgcac agaacgaata cgaagcctgt tggaacgtca agccagagag attgaagctt   2700
ttgactctga aagcatgaga ctaggtttta gtaatatggt cctttctaat ctctcccctg   2760
aggcattcag ccacagctac ccgggagctt ctggttggtc acacaaccct actgggggtc   2820
caggacctca ctggggtcat cccatggggtg gcccaccaca agcttggggc catccaatgc   2880
aaggtggacc ccagccatgg ggtcacccctt cagggccaat gcaagggggta cctcgaggta   2940 gcagtatggg agtccgcaat agccccccagg ctctgaggcg gacagcttct ggggggacgga   3000 cagagcaggg catgagcaga agcacgagtg tcacttcaca aatatccaat gggtcacaca   3060
tgtcttatac ataacttaat aattgagagt ggcaattccg ctggagctgt ctgccaaaag   3120
aaactgccta cagacatcat cacagcagcc tcctcacttg ggtactacag tgtggaagct   3180
gagtgcatat ggtatatttt attcattttt gtaaagcgtt ctgttttgtg tttactaatt   3240
gggatgtcat agtacttggc tgccgggttt gtttgttttt ggggaaattt tgaaaagtgg   3300
agttgatatt aaaaataaat gtgtatgtgt gtacatatat atacacacac atacacatat   3360
attatgcatg tggtgaaaag aattggctag ataggggattt tttctgaaca ctgcaaaaat    3420
agaacgtagc aaaatggctt cagttatcac ttttgggtgt ctgtatccta agaagtttct   3480
gaaaagatct aaagcctttt tatcccatat cccaaattct tatgagccac tcacagcagg   3540
cagcatatgt tgaaataagt tattactggt acacacctgc attgcctcac cagtgtattt   3600
atttgttatt aaattgatct gacttctcag cctcatttgg actaaaaaaa gaaagcagaa   3660
atccatgaac acattgcttc tcggccttttt ggctaagatc aagtgtagaa atccatgaac   3720
actaaaggac ttcattgatt ttttcagaga gtagaaaaca acttagtttt tcttttttcc   3780
tgaatgcgtc ataggcttgt gagtgatttt tgtccattca attgtgcctt ctttgtatta   3840
tgataagatg ggggtactta aggagatcac aagttgtgtg aggattgcat taacaaacct   3900
atgagccttc aatggggaag accagaaggg tgagaggggc cctgaaagtt catatggtgg   3960
gtatgtcccg cagcagagtg aggagatgaa gcttacgtgt cctgacgttt tgttgcttat   4020
actgtgatat ctcatcctag ctaagctcta taatgcccaa gaccccaaac agtacttttta  4080 ctttgtttgt acaaaaacaa agacatatag ccaatacaaa tcaaatgccg gaggtgtttg   4140
```

| | | | | |
|---|---|---|---|---|
| atgccatatt | tgcaaattgc | catctattga | aattctcgtc | acactacata gacataattg | 4200 |
| ttatctcctt | ttggcttatg | tgattttctg | tttacaagta | gaatagccaa ttatttaaat | 4260 |
| gtttagttgc | cacagtgaac | caggagtcac | tgagccaatg | actttaccag ctgctgacta | 4320 |
| atcttcatca | ccactgtaga | ttttgctgca | tgtgcaggtc | ctctattttt aattgctgtt | 4380 |
| ttcgttgctg | cagtacttta | caaacttcta | gttcgttgag | acttagtgac catttggcat | 4440 |
| caagttaaca | tcacacaata | ggaaacacca | cttccacaag | tctcaagcct cagtgctaaa | 4500 |
| gtactactga | aaaggaacta | ggaagtttgg | ccaatt | | 4536 |

<210> SEQ ID NO 12
<211> LENGTH: 4535
<212> TYPE: DNA
<213> ORGANISM: Homo sapiens

<400> SEQUENCE: 12

| | | | | | |
|---|---|---|---|---|---|
| tacagatgaa | ccaaggatcg | ggatagcagt | ataaaattag | aatcaagaca gctgactgct | 60 |
| cagcaggatg | ccatcaacta | acagagcagg | cagcctgaag | gaccctgaaa ttgcagagct | 120 |
| cttcttcaaa | gaagatccag | agaagctctt | cacagatctc | agagaaattg gccatggaag | 180 |
| ctttggagca | gtgtattttg | cacgagatgt | gcgtaccaat | gaagtggtgg ccatcaagaa | 240 |
| aatgtcttat | agtggaaagc | agtctactga | gaaatggcag | gatattatta aggaagtcaa | 300 |
| gtttctacaa | agaataaaac | atcccaacag | tatagaatac | aaaggctgtt atttacgtga | 360 |
| acacacagca | tggcttgtaa | tggaatattg | tttaggatct | gcttcggatt tactagaagt | 420 |
| tcacaaaaag | ccattacaag | aagtggaaat | agcagcaatt | acacatggtg ctcttcaggg | 480 |
| attagcctac | ttacattctc | atactatgat | tcatagagat | atcaaagcag gaaatatcct | 540 |
| tctgacagaa | ccaggccagg | tgaaacttgc | tgactttggc | tctgcttcca tggcatcacc | 600 |
| tgccaattcc | tttgtgggaa | cgccgtattg | gatggcccca | gaagtaattt tagccatgga | 660 |
| tgaaggacaa | tatgatggca | agtagatgt | gtggtctctt | ggaataacat gtattgaact | 720 |
| agcggaaagg | aagcctcctt | tatttaatat | gaatgcaatg | agtgcctat atcacatagc | 780 |
| ccaaaatgaa | tcccctacac | tacagtctaa | tgaatggtct | gattattttc gcaactttgt | 840 |
| agattcttgc | ctccagaaaa | tccctcaaga | tcgacctaca | tcagaggaac ttttaaagca | 900 |
| catatttgtt | cttcgggagc | gccctgaaac | cgtgttaata | gatctcattc agaggacaaa | 960 |
| ggatgcagta | agagagctgg | acaatctgca | gtatcgaaag | atgaagaaac tccttttcca | 1020 |
| ggaggcacat | aatggaccag | cagtagaagc | acaggaagaa | gaagaggaac aagatcatgg | 1080 |
| tgttggccgg | acaggaacag | ttaatagtgt | tggaagtaat | caatccattc ccagcatgtc | 1140 |
| catcagtgcc | agcagccaaa | gcagtagtgt | taacagtctt | ccagatgtct cagatgacaa | 1200 |
| gagtgagcta | acatgatgg | agggagacca | cacagtgatg | tctaacagtt ctgttatcca | 1260 |
| tttaaaacca | gaggaagaaa | attacagaga | agagggagat | cctagaacaa gagcatcaga | 1320 |
| tccacaatct | ccaccccaag | tatctcgtca | caaatcacac | tatcgtaatc gagaacactt | 1380 |
| tgctactata | cggacagcat | cactggttac | gaggcaaatg | caagaacatg agcaggactc | 1440 |
| tgagcttaga | gaacaaatgt | ctggctataa | gcgaatgagg | cgacaacatc aaaagcaact | 1500 |
| gatgactctg | gaaaacaagc | taaggctga | gatggatgaa | catcgcctca gattagaaa | 1560 |
| agatcttgaa | actcagcgta | acaattttgc | tgcagaaatg | gagaaactta tcaagaaaca | 1620 |
| ccaggctgcc | atggagaaag | aggctaaagt | gatgtccaat | gaagagaaaa atttcagca | 1680 |
| acatattcag | gcccaacaga | agaaagaact | gaatagtttt | ctcgagtccc agaaaagaga | 1740 |

-continued

```
gtataaactt cgaaaagagc agcttaaaga ggagctaaat gaaaaccaga gtaccccccaa   1800 aaaagaaaaa caggagtggc tttcaaagca gaaggagaat atacagcatt ccaagcaga    1860 agaagaagct aaccttcttc gacgtcaaag acaataccta gagctggaat gccgtcgctt   1920
caagagaaga atgttacttg ggcgtcataa cttagagcag gaccttgtca gggaggagtt   1980
aaacaaaaga cagactcaga aggacttaga gcatgccatg ctactccgac agcatgaatc   2040
tatgcaagaa ctggagttcc gccacctcaa cacaattcag aagatgcgct gtgagttgat   2100
cagattacag catcaaactg agctcactaa ccagctggaa tataataagc gaagagaacg   2160
agaactaaga cgaaagcatg tcatggaagt tcgacaacag cctaagagtt tgaagtctaa   2220
agaactccaa ataaaaagc agtttcagga tacctgcaaa atccaaacca gacagtacaa    2280
agcattaaga aatcacctgc tggagactac accaaagagt gagcacaaag ctgttctgaa   2340
acggctcaag gaggaacaga cccggaaatt agctatcttg gctgagcagt atgatcacag   2400
cattaatgaa atgctctcca cacaagccct gcgtttggat gaagcacagg aagcagagtg   2460
ccaggttttg aagatgcagc tgcagcagga actggagctg ttgaatgcgt atcagagcaa   2520
aatcaagatg caagctgagg cacaacatga tcgagagctt cgcgagcttg aacagagggt   2580
ctccctccgg agggcactct tagaacaaaa gattgaagaa gagatgttgg ctttgcagaa   2640
tgagcgcaca gaacgaatac gaagcctgtt ggaacgtcaa gccagagaga ttgaagcttt   2700
tgactctgaa agcatgagac taggttttag taatatggtc ctttctaatc tctcccctga   2760
ggcattcagc cacagctacc cgggagcttc tggttggtca cacaaccccta ctgggggtcc   2820 aggacctcac tggggtcatc ccatgggtgg cccaccacaa gcttggggcc atccaatgca   2880
aggtggaccc cagccatggg gtcacccttc agggccaatg caaggggtac ctcgaggtag   2940
cagtatggga gtccgcaata gccccaggc tctgaggcgg acagcttctg ggggacggac    3000
ggagcagggc atgagcagaa gcacgagtgt cacttcacaa atatccaatg gtcacacat    3060 gtcttataca taacttaata attgagagtg gcaattccgc tggagctgtc tgccaaaaga   3120
aactgcctac agacatcatc acagcagcct cctcacttgg gtactacagt gtggaagctg   3180
agtgcatatg gtatatttta ttcattttttg taaagcgttc tgttttgtgt ttactaattg   3240
ggatgtcata gtacttggct gccgggtttg tttgttttttg gggaattttt gaaaagtgga   3300
gttgatatta aaaataaatg tgtatgtgtg tacatatata tacacacaca tacacatata    3360
ttatgcatgt ggtgaaaaga attggctaga tagggggattt ttctgaacac tgcaaaaata   3420
gaacgtagca aaatggcttc agttatcact tttgggtgtc tgtatcctaa gaagtttctg   3480
aaaagatcta aagcctttttt atcccatatc ccaaattctt atgagccact cacagcaggc   3540
agcatatgtt gaaataagtt attactggta cacacctgca ttgcctcacc agtgtattta   3600
tttgttatta aattgatctg acttctcagc ctcatttgga ctaaaaaaag aaagcagaaa   3660
tccatgaaca cattgcttct cggccttttg gctaagatca agtgtagaaa tccatgaaca   3720
ctaaaggact tcattgattt tttcagagag tagaaaacaa cttagttttt ctttttttcct   3780 gaatgcgtca taggcttgtg agtgattttt gtccattcaa ttgtgccttc tttgtattat    3840
gataagatgg gggtacttaa ggagatcaca agttgtgtga ggattgcatt aacaaaccta   3900
tgagccttca atgggggaaga ccagaagggt gagaggggcc ctgaaagttc atatggtggg   3960
tatgtcccgc agcagagtga ggagatgaag cttacgtgtc ctgacgtttt gttgcttata   4020
ctgtgatatc tcatcctagc taagctctat aatgcccaag accccaaaca gtactttttac   4080 tttgtttgta caaaaacaaa gacatatagc caatacaaat caaatgccgg aggtgtttga   4140
```

| | |
|---|---:|
| tgccatattt gcaaattgcc atctattgaa attctcgtca cactacatag acataattgt | 4200 |
| tatctccttt tggcttatgt gattttctgt ttacaagtag aatagccaat tatttaaatg | 4260 |
| tttagttgcc acagtgaacc aggagtcact gagccaatga ctttaccagc tgctgactaa | 4320 |
| tcttcatcac cactgtagat tttgctgcat gtgcaggtcc tctatttta attgctgttt | 4380 |
| tcgttgctgc agtactttac aaacttctag ttcgttgaga cttagtgacc atttggcatc | 4440 |
| aagttaacat cacacaatag gaaacaccac ttccacaagt ctcaagcctc agtgctaaag | 4500 |
| tactactgaa aaggaactag gaagtttggc caatt | 4535 |

<210> SEQ ID NO 13
<211> LENGTH: 3003
<212> TYPE: DNA
<213> ORGANISM: Homo sapiens

<400> SEQUENCE: 13

| | |
|---|---:|
| atgccatcaa ctaacagagc aggcagtctt aaggaccctg aaattgcaga gctcttcttc | 60 |
| aaagaagatc cagagaagct cttcacagat ctcagagaaa ttggccatgg aagctttgga | 120 |
| gcagtgtatt ttgcacgaga gtgtcgtacc aatgaagtgg tggccatcaa gaaaatgtct | 180 |
| tatagtggaa agcagtctac tgagaaatgg caggatatta ttaaggaagt caagtttcta | 240 |
| caaagaataa aacatcccaa cagtatagaa tacaaaggct gttatttacg tgaacacaca | 300 |
| gcatggcttg taatggaata ttgtttagga tctgcttcgg atttactaga agttcacaaa | 360 |
| aagccattac aagaagtgga aatagcagca attacacatg gtgctcttca gggattagcc | 420 |
| tacttacatt ctcatactat gattcataga gatatcaaag caggaaatat ccttctgaca | 480 |
| gaaccaggcc aggtgaaact tgctgacttt ggctctgctt ccatggcatc acctgccaat | 540 |
| tcctttgtgg gaacgccgta ttggatggcc ccagaagtaa ttttagccat ggatgaagga | 600 |
| caatatgatg gcaaagtaga tgtgtggtct cttggaataa catgtattga actagcggaa | 660 |
| aggaagcctc ctttatttaa tatgaatgca atgagtgcct tatatcacat agcccaaaat | 720 |
| gaatcccta cactacagtc taatgaatgg tctgattatt ttcgcaactc tgtagattct | 780 |
| tgcctccaga aaatccctca agatcgacct acatcagagg aacttttaaa gcacatattt | 840 |
| gttcttcggg agcgccctga aaccgtgtta atagatctca ttcagaggac aaaggatgca | 900 |
| gtaagagagc tggacaatct gcagtatcga agatgaaga aactcctttt ccaggaggca | 960 |
| cataatggac cagcagtaga agcacaggaa gaagaagagg aacaagatca tggtgttggc | 1020 |
| cggacaggaa cagttaatag tgttggaagt aatcaatcca ttcccagcat gtccatcagt | 1080 |
| gccagcagcc aaagcagtag tgttaacagt cttccagatg tctcagatga caagagtgag | 1140 |
| ctagacatga tggagggaga ccacacagtg atgtctaaca gttctgttat ccatttaaaa | 1200 |
| ccagaggaag aaaattacag agaagaggga gatcctagaa caagagcatc agatccacaa | 1260 |
| tctccacccc aagtatctcg tcacaaatca cactatcgta atcgagaaca ctttgctact | 1320 |
| atacggacag catcactggt tacgaggcaa atgcaagaac atgagcagga ctctgagctt | 1380 |
| agagaacaaa tgtctggcta taagcgaatg aggcgacaac atcaaaagca actgatgact | 1440 |
| ctggaaaaca gctaaaggc tgagatggat gaacatcgcc tcagattaga caaagatctt | 1500 |
| gaaactcagc gtaacaattt tgctgcagaa atggagaaac ttatcaagaa acaccaggct | 1560 |
| gctatggaga aagaggctaa agtgatgtcc aatgaagaga aaaatttca gcaacatatt | 1620 |
| caggcccaac agaagaaaga actgaatagt tttctcgagt cccagaaaag agagtataaa | 1680 |
| cttcgaaaag agcagcttaa agaggagcta aatgaaaacc agagtacccc caaaaaagaa | 1740 |

-continued

| | |
|---|---|
| aaacaggagt ggctttcaaa gcagaaggag aatatacagc atttccaagc agaagaagaa | 1800 |
| gctaaccttc ttcgacgtca aagacaatac ctagagctgg aatgccgtcg cttcaagaga | 1860 |
| agaatgttac ttgggcgtca taacttagag caggaccttg tcagggagga gttaaacaaa | 1920 |
| agacagactc agaaggactt agagcatgcc atgctactcc gacagcatga atctatgcaa | 1980 |
| gaactggagt tccgccacct caacacaatt cagaagatgc gctgtgagtt gatcagatta | 2040 |
| cagcatcaaa ctgagctcac taaccagctg aatataata agcgaagaga acgaaacta | 2100 |
| agacgaaagc atgtcatgga agttcgacaa cagcctaaga gtttgaagtc taagaactc | 2160 |
| caaataaaaa agcagtttca ggatacctgc aaaatccaaa ccagacagta caaagcatta | 2220 |
| agaaatcacc tgttggagac tacaccaaag agtgagcaca agctgttct gaaacggctc | 2280 |
| aaggaggaac agaccggaa attagctatc ttggctgagc agtatgatca cagcattaat | 2340 |
| gaaatgctct ccacacaagc cctgcgtttg atgaagcac aggaagcaga gtgccaggtt | 2400 |
| ttgaagatgc agctgcagca ggaactggag ctgttgaatg cgtatcagag caaaatcaag | 2460 |
| atgcaagctg aggcacaaca tgatcgagag cttcgcgagc ttgaacagag ggtctccctc | 2520 |
| cggagggcac tcttagaaca aaagattgaa gaagagatgt tggctttgca gaatgagtgc | 2580 |
| acagaacgaa tacgaagcct gttggaacgt caagccagag agattgaagc ttttgactct | 2640 |
| gaaagcatga gactaggttt tagtaatatg gtcctttcta atctctcccc tgaggcattc | 2700 |
| agccacagct acccgggagc ttctggttgg tcacacaacc ctactggggg tccaggacct | 2760 |
| cactggggtc atcccatggg tggcccacca caagcttggg gccatccaat gcaaggtgga | 2820 |
| ccccagccat ggggtcaccc ttcagggcca atgcaagggg tacctcgagg tagcagtatg | 2880 |
| ggagtccgca atagcccca ggctctgagg cggacagctt ctgggggacg gacagagcag | 2940 |
| ggcatgagca gaagcacgag tgtcacttca caaatatcca atgggtcaca catgtcttat | 3000 |
| aca | 3003 |

<210> SEQ ID NO 14
<211> LENGTH: 3048
<212> TYPE: DNA
<213> ORGANISM: Homo sapiens

<400> SEQUENCE: 14

| | |
|---|---|
| tgctcagcag gatgccatca actaacagag caggcagcct gaaggaccct gaaattgcag | 60 |
| agctcttctt caaagaagat ccagagaagc tcttcacaga tctcagagaa attggccatg | 120 |
| gaagctttgg agcagtgtat tttgcacgag atgtgcgtac caatgaagtg gtggccatca | 180 |
| agaaaatgtc ttatagtgga aagcagtcta ctgagaaatg gcaggatatt attaaggaag | 240 |
| tcaagtttct acaagaata aaacatccca acagtataga atacaaaggc tgttatttac | 300 |
| gtgaacacac agcatggctt gtaatggaat attgtttagg atctgcttcg gatttactag | 360 |
| aagttcacaa aaagccatta caagaagtgg aaatagcagc aattacacat ggtgctcttc | 420 |
| agggattagc ctacttacat tctcatacta tgattcatag agatatcaaa gcaggaaata | 480 |
| tccttctgac agaaccaggc caggtgaaac ttgctgactt ggctctgct tccatggcat | 540 |
| cacctgccaa ttcctttgtg ggaacgccgt attggatggc cccagaagta attttagcca | 600 |
| tggatgaagg acaatatgat ggcaaagtag atgtgtggtc tcttggaata acatgtattg | 660 |
| aactagcgga aggaagcct ccttttattta atatgaatgc aatgagtgcc ttatatcaca | 720 |
| tagcccaaaa tgaatcccct acactacagt ctaatgaatg gtctgattat tttcgcaact | 780 |
| ttgtagattc ttgcctccag aaaatccctc aagatcgacc tacatcagag gaactttaa | 840 |

-continued

```
agcacatatt tgttcttcgg gagcgccctg aaaccgtgtt aatagatctc attcagagga      900
caaaggatgc agtaagagag ctggacaatc tgcagtatcg aaagatgaag aaactccttt      960
tccaggaggc acataatgga ccagcagtag aagcacagga agaagaagag gaacaagatc     1020
atggtgttgg ccggacagga acagttaata gtgttggaag taatcaatcc attcccagca     1080
tgtccatcag tgccagcagc caaagcagta gtgttaacag tcttccagat gtctcagatg     1140
acaagagtga gctagacatg atggagggag accacacagt gatgtctaac agttctgtta     1200
tccatttaaa accagaggaa gaaaattaca gagaagaggg agatcctaga caagagcat      1260
cagatccaca atctccaccc caagtatctc gtcacaaatc acactatcgt aatcgagaac     1320
actttgctac tatacggaca gcatcactgg ttacgaggca aatgcaagaa catgagcagg     1380
actctgagct tagagaacaa atgtctggct ataagcgaat gaggcgacaa catcaaaagc     1440
aactgatgac tctggaaaac aagctaaagg ctgagatgga tgaacatcgc ctcagattag     1500
acaaagatct tgaaactcag cgtaacaatt ttgctgcaga aatggagaaa cttatcaaga     1560
aacaccaggc tgctatggag aaagaggcta agtgatgtc caatgaagag aaaaaatttc      1620
agcaacatat tcaggcccaa cagaagaaag aactgaatag ttttctcgag tcccagaaaa     1680
gagagtataa acttcgaaaa gagcagctta agaggagct aaatgaaaac cagagtaccc      1740
ccaaaaaaga aaaacaggag tggctttcaa agcagaagga gaatatacag catttccaag     1800
cagaagaaga agctaacctt cttcgacgtc aaagacaata cctagagctg gaatgccgtc     1860
gcttcaagag aagaatgtta cttgggcgtc ataacttaga gcaggacctt gtcagggagg     1920
agttaaacaa aagacagact cagaaggact tagagcatgc catgctactc cgacagcatg     1980
aatctatgca agaactggag ttccgccacc tcaacacaat tcagaagatg cgctgtgagt     2040
tgatcagatt acagcatcaa actgagctca ctaaccagct ggaatataat aagcgaagag     2100
aacgagaact aagacgaaag catgtcatgg aagttcgaca acagcctaag agtttgaagt     2160
ctaaagaact ccaaataaaa aagcagtttc aggatacctg caaaatccaa accagacagt     2220
acaaagcatt aagaaatcac ctgctggaga ctacaccaaa gagtgagcac aaagctgttc     2280
tgaaacggct caaggaggaa cagacccgga aattagctat cttggctgag cagtatgatc     2340
acagcattaa tgaaatgctc tccacacaag ccctgcgttt ggatgaagca caggaagcag     2400
agtgccaggt tttgaagatg cagctgcagc aggaactgga gctgttgaat gcgtatcaga     2460
gcaaaatcaa gatgcaagct gaggcacaac atgatcgaga gcttcgcgag cttgaacaga     2520
gggtctccct ccggagggca ctcttagaac aaaagattga agaagagatg ttggctttgc     2580
agaatgagcg cacagaacga atacgaagcc tgttggaacg tcaagccaga gagattgaag     2640
cttttgactc tgaaagcatg agactaggtt ttagtaatat ggtcctttct aatctctccc     2700
ctgaggcatt cagccacagc tacccgggag cttctggttg gtcacacaac cctactgggg     2760
gtccaggacc tcactgggt catcccatgg gtggcccacc acaagcttgg ggccatccaa      2820
tgcaaggtgg accccagcca tggggtcacc cttcagggcc aatgcaaggg gtacctcgag     2880
gtagcagtat gggagtccgc aatagccccc aggctctgag gcggacagct tctggggac      2940
ggacagagca gggcatgagc agaagcacga gtgtcacttc acaaatatcc aatgggtcac     3000
acatgtctta tacataactt aataattgag agtggcaatt ccgctgga                  3048
```

<210> SEQ ID NO 15
<211> LENGTH: 3148
<212> TYPE: DNA
<213> ORGANISM: Homo sapiens

<400> SEQUENCE: 15

```
ggcacgaggg tggcgccggg cggcggggtc ctgcgtggag agtgggacgc aacgccgaga    60
ccgcgagcag aggctgcgca cagccggatc cggcactcag cgaccggacc caaggatccg   120
ccggggaaca agccacagga gagcgactca ggaacaagtg tgggagagga gcggcggcg    180
gcggcgccgg gcccgggggt ggtgacagca ggtctgaggt tgcatcataa atacaaagga   240
ctgaagttat aaaagagaaa agagaagttt gctgctaaaa tgaatctgag caatatggaa   300
tattttgtgc cacacacaaa aaggtactga agatttaccc cccaaaaaaa attgtcaatg   360
agaaataaag ctaactgata tcaaaaagca gagcctgctc tactggccat catgcgtaaa   420
ggggtgctga aggacccaga gattgccgat ctattctaca aagatgatcc tgaggaactt   480
tttattggtt tgcatgaaat tggacatgga agttttggag cagtttattt tgctacaaat   540
gctcacacca gtgaggtggt ggcaattaag aagatgtcct atagtgggaa gcagacccat   600
gagaaatggc aagatattct taaggaagtt aaattttttac gacaattgaa gcatcctaat   660
actattgagt acaaaggctg ttacttgaaa gaacacactg cttggttggt gatggaatat   720
tgcttaggct cagcctctga tttattagaa gttcataaaa aaccacttca ggaagtggag   780
atcgctgcca ttactcatgg agccttgcat ggactagcct acctacattc tcatgcattg   840
attcataggg atattaaagc aggaaatatt cttctaacag agccaggtca ggtaaaacta   900
gctgattttg gatctgcttc aatggcttct cctgccaact ccttcgtggg cacaccttac   960
tggatggctc cagaggtgat cttagctatg atgaaggac agtatgatgg aaagttgat   1020
atttggtcac ttggcatcac ttgtattgaa ttggcggaac ggaagccgcc ccttttcaac  1080
atgaatgcaa tgagtgcctt atatcacatt gcccagaatg actccccaac gttacagtct  1140
aatgaatgga cagactcctt taggagattt gttgattact gcttgcagaa atacctcag  1200
gaaaggccaa catcagcaga actattaagg catgactttg ttcgacgaga ccggccacta  1260
cgtgtcctca ttgacctcat acagaggaca aaagatgcag ttcgtgagct agataaccta  1320
cagtaccgaa aaatgaaaaa atacttttc caagagacac ggaatggacc cttgaatgag  1380
tcacaggagg atgaggaaga cagtgaacat ggaaccagcc tgaacaggga atggacagc   1440
ctgggcagca accattccat tccaagcatg tccgtgagca caggcagcca gagcagcagt  1500
gtgaacagca tgcaggaagt catggacgag agcagttccg aacttgtcat gatgcacgat  1560
gacgaaagca caatcaattc cagctcctcc gtcgtgcata agaaagatca tgtattcata  1620
agggatgagg cgggccacgg cgatcccagg cctgagccgc ggcctaccca gtcagttcag  1680
agccaggccc tccactaccg gaacagagag cgctttgcca cgatcaaatc agcatctttg  1740
gttacacgac agatccatga gcatgagcag gagaacgagt tgcgggaaca gatgtcaggt  1800
tataagcgga tgcggcgcca gcaccagaag cagctgatcg ccctggagaa caagctgaag  1860
gctgagatgg acgagcaccg cctcaagcta cagaaggagg tggagacgca tgccaacaac  1920
tcgtccatcg agctggagaa gctggccaag aagcaagtgg ctatcataga aaaggaggca  1980
aaggtagctg cagcagatga agaagttc cagcaacaga tcttggccca gcagaagaaa  2040
gatttgacaa cttcttaga aagtcagaag aagcagtata agatttgtaa ggaaaaaata  2100
aaagaggaaa tgaatgagga ccatagcaca cccaagaaag agaagcaaga gcggatctcc  2160
aaacataag agaacttgca gcacacacag gctgaagagg aagcccacct tctcactcaa  2220
cagagactgt actacgacaa aaattgtcgt ttcttcaagc ggaaaataat gatcaagcgg  2280
cacgaggtgg agcagcagaa cattcgggag gaactaaata aaaagaggac ccagaaggag  2340
```

-continued

```
atggagcatg ccatgctaat ccggcacgac gagtccaccc gagagctaga gtacaggcag    2400
ctgcacacgt tacagaagct acgcatggat ctgatccgtt tacagcacca gacggaactg    2460
gaaaaccagc tggagtacaa taagaggcga gaaagagaac tgcacagaaa gcatgtcatg    2520
gaacttcggc aacagccaaa aaacttaaag gccatggaaa tgcaaattaa aaaacagttt    2580
caggacactt gcaaagtaca gaccaaacag tataaagcac tcaagaatca ccagttggaa    2640
gttactccaa agaatgagca caaaacaatc ttaaagacac tgaaagatga gcagacaaga    2700
aaacttgcca ttttggcaga gcagtatgaa cagagtataa atgaaatgat ggcctctcaa    2760
gcgttacggc tagatgaggc tcaagaagca gaatgccagg ccttgaggct acagctccag    2820
caggaaatgg agctgctcaa cgcctaccag agcaaaatca gatgcaaac agaggcacaa    2880 catgaacgtg agctccagaa gctagagcag agagtgtctc tgcgcagagc acaccttgag    2940
cagaagattg aagaggagct ggctgccctt cagaaggaac gcagcgagag aataaagaac    3000
ctattggaaa ggcaagagcg agagattgaa acttttgaca tggagagcct cagaatggga    3060
tttgggaatt tggttacatt agatttttcct aaggaggact acagatgaga ttaaattttt    3120
tgccatttac aaaaaaaaaa aaaaaaaa                                       3148
```

<210> SEQ ID NO 16
<211> LENGTH: 1049
<212> TYPE: PRT
<213> ORGANISM: Homo sapiens

<400> SEQUENCE: 16

```
Met Pro Ala Gly Gly Arg Ala Gly Ser Leu Lys Asp Pro Asp Val Ala
1               5                   10                  15

Glu Leu Phe Phe Lys Asp Asp Pro Glu Lys Leu Phe Ser Asp Leu Arg
            20                  25                  30

Glu Ile Gly His Gly Ser Phe Gly Ala Val Tyr Phe Ala Arg Asp Val
        35                  40                  45

Arg Asn Ser Glu Val Val Ala Ile Lys Lys Met Ser Tyr Ser Gly Lys
    50                  55                  60

Gln Ser Asn Glu Lys Trp Gln Asp Ile Ile Lys Glu Val Arg Phe Leu
65                  70                  75                  80

Gln Lys Leu Arg His Pro Asn Thr Ile Gln Tyr Arg Gly Cys Tyr Leu
                85                  90                  95

Arg Glu His Thr Ala Trp Leu Val Met Glu Tyr Cys Leu Gly Ser Ala
            100                 105                 110

Ser Asp Leu Leu Glu Val His Lys Lys Pro Leu Gln Glu Val Glu Ile
        115                 120                 125

Ala Ala Val Thr His Gly Ala Leu Gln Gly Leu Ala Tyr Leu His Ser
    130                 135                 140

His Asn Met Ile His Arg Asp Val Lys Ala Gly Asn Ile Leu Leu Ser
145                 150                 155                 160

Glu Pro Gly Leu Val Lys Leu Gly Asp Phe Gly Ser Ala Ser Ile Met
                165                 170                 175

Ala Pro Ala Asn Ser Phe Val Gly Thr Pro Tyr Trp Met Ala Pro Glu
            180                 185                 190

Val Ile Leu Ala Met Asp Glu Gly Gln Tyr Asp Gly Lys Val Asp Val
        195                 200                 205

Trp Ser Leu Gly Ile Thr Cys Ile Glu Leu Ala Glu Arg Lys Pro Pro
    210                 215                 220

Leu Phe Asn Met Asn Ala Met Ser Ala Leu Tyr His Ile Ala Gln Asn
225                 230                 235                 240
```

-continued

Glu Ser Pro Val Leu Gln Ser Gly His Trp Ser Glu Tyr Phe Arg Asn
            245                 250                 255

Phe Val Asp Ser Cys Leu Gln Lys Ile Pro Gln Asp Arg Pro Thr Ser
            260                 265                 270

Glu Val Leu Lys His Arg Phe Val Leu Arg Glu Pro Pro Thr
            275                 280                 285

Val Ile Met Asp Leu Ile Gln Arg Thr Lys Asp Ala Val Arg Glu Leu
            290                 295                 300

Asp Asn Leu Gln Tyr Arg Lys Met Lys Lys Ile Leu Phe Gln Glu Ala
305                 310                 315                 320

Pro Asn Gly Pro Gly Ala Glu Ala Pro Glu Glu Glu Glu Ala Glu
                325                 330                 335

Pro Tyr Met His Arg Ala Gly Thr Leu Thr Ser Leu Glu Ser Ser His
            340                 345                 350

Ser Val Pro Ser Met Ser Ile Ser Ala Ser Ser Gln Ser Ser Ser Val
            355                 360                 365

Asn Ser Leu Ala Asp Ala Ser Asp Asn Glu Glu Glu Glu Glu Glu
            370                 375                 380

Glu Glu Glu Glu Glu Glu Glu Gly Pro Glu Ala Arg Glu Met Ala
385                 390                 395                 400

Met Met Gln Glu Gly Glu His Thr Val Thr Ser His Ser Ser Ile Ile
                405                 410                 415

His Arg Leu Pro Gly Ser Asp Asn Leu Tyr Asp Asp Pro Tyr Gln Pro
            420                 425                 430

Glu Ile Thr Pro Ser Pro Leu Gln Pro Pro Ala Ala Pro Ala Pro Thr
            435                 440                 445

Ser Thr Thr Ser Ser Ala Arg Arg Arg Ala Tyr Cys Arg Asn Arg Asp
            450                 455                 460

His Phe Ala Thr Ile Arg Thr Ala Ser Leu Val Ser Arg Gln Ile Gln
465                 470                 475                 480

Glu His Glu Gln Asp Ser Ala Leu Arg Glu Gln Leu Ser Gly Tyr Lys
                485                 490                 495

Arg Met Arg Arg Gln His Gln Lys Gln Leu Leu Ala Leu Glu Ser Arg
            500                 505                 510

Leu Arg Gly Glu Arg Glu Glu His Ser Ala Arg Leu Gln Arg Glu Leu
            515                 520                 525

Glu Ala Gln Arg Ala Gly Phe Gly Ala Glu Ala Glu Lys Leu Ala Arg
            530                 535                 540

Arg His Gln Ala Ile Gly Glu Lys Glu Ala Arg Ala Ala Gln Ala Glu
545                 550                 555                 560

Glu Arg Lys Phe Gln Gln His Ile Leu Gly Gln Lys Lys Glu Leu
                565                 570                 575

Ala Ala Leu Leu Glu Ala Gln Lys Arg Thr Tyr Lys Leu Arg Lys Glu
            580                 585                 590

Gln Leu Lys Glu Glu Leu Gln Glu Asn Pro Ser Thr Pro Lys Arg Glu
            595                 600                 605

Lys Ala Glu Trp Leu Leu Arg Gln Lys Glu Gln Leu Gln Gln Cys Gln
            610                 615                 620

Ala Glu Glu Glu Ala Gly Leu Leu Arg Arg Gln Arg Gln Tyr Phe Glu
625                 630                 635                 640

Leu Gln Cys Arg Gln Tyr Lys Arg Lys Met Leu Leu Ala Arg His Ser
                645                 650                 655

Leu Asp Gln Asp Leu Leu Arg Glu Asp Leu Asn Lys Lys Gln Thr Gln

```
                     660                 665                 670
Lys Asp Leu Glu Cys Ala Leu Leu Arg Gln His Glu Ala Thr Arg
            675                 680                 685

Glu Leu Glu Leu Arg Gln Leu Gln Ala Val Gln Arg Thr Arg Ala Glu
        690                 695                 700

Leu Thr Arg Leu Gln His Gln Thr Glu Leu Gly Asn Gln Leu Glu Tyr
705                 710                 715                 720

Asn Lys Arg Arg Glu Gln Glu Leu Arg Gln Lys His Ala Ala Gln Val
                725                 730                 735

Arg Gln Gln Pro Lys Ser Leu Lys Ser Lys Glu Leu Gln Ile Lys Lys
            740                 745                 750

Gln Phe Gln Glu Thr Cys Lys Ile Gln Thr Arg Gln Tyr Lys Ala Leu
        755                 760                 765

Arg Ala His Leu Leu Glu Thr Thr Pro Lys Ala Gln His Lys Ser Leu
    770                 775                 780

Leu Lys Arg Leu Lys Glu Glu Gln Thr Arg Lys Leu Ala Ile Leu Ala
785                 790                 795                 800

Glu Gln Tyr Asp Gln Ser Ile Ser Glu Met Leu Ser Ser Gln Ala Leu
                805                 810                 815

Arg Leu Asp Glu Thr Gln Glu Ala Glu Phe Gln Ala Leu Arg Gln Gln
            820                 825                 830

Leu Gln Gln Glu Leu Glu Leu Asn Ala Tyr Gln Ser Lys Ile Lys
        835                 840                 845

Ile Arg Thr Glu Ser Gln His Glu Arg Glu Leu Arg Glu Leu Glu Gln
    850                 855                 860

Arg Val Ala Leu Arg Arg Ala Leu Leu Glu Gln Arg Val Glu Glu Glu
865                 870                 875                 880

Leu Leu Ala Leu Gln Thr Gly Arg Ser Glu Arg Ile Arg Ser Leu Leu
                885                 890                 895

Glu Arg Gln Ala Arg Glu Ile Glu Ala Phe Asp Ala Gly Ser Met Arg
            900                 905                 910

Leu Gly Phe Ser Ser Met Ala Leu Gly Gly Ile Pro Ala Glu Ala Ala
        915                 920                 925

Ala Gln Gly Tyr Pro Ala Pro Pro Ala Pro Ala Trp Pro Ser Arg
    930                 935                 940

Pro Val Pro Arg Ser Gly Ala His Trp Ser His Gly Pro Pro Pro
945                 950                 955                 960

Gly Met Pro Pro Ala Trp Arg Gln Pro Ser Leu Leu Ala Pro Pro
                965                 970                 975

Gly Pro Pro Asn Trp Leu Gly Pro Thr Gln Ser Gly Thr Pro Arg
            980                 985                 990

Gly Gly Ala Leu Leu Leu Leu Arg Asn Ser Pro Gln Pro Leu Arg Arg
        995                 1000                 1005

Ala Ala Ser Gly Gly Ser Gly Ser Glu Asn Val Gly Pro Pro Ala
    1010                 1015                 1020

Ala Ala Val Pro Gly Pro Leu Ser Arg Ser Thr Ser Val Ala Ser
    1025                 1030                 1035

His Ile Leu Asn Gly Ser Ser His Phe Tyr Ser
    1040                 1045
```

<210> SEQ ID NO 17
<211> LENGTH: 898
<212> TYPE: PRT
<213> ORGANISM: Homo sapiens -continued

<400> SEQUENCE: 17

```
Met Arg Lys Gly Val Leu Lys Asp Pro Glu Ile Ala Asp Leu Phe Tyr
1               5                   10                  15

Lys Asp Asp Pro Glu Glu Leu Phe Ile Gly Leu His Glu Ile Gly His
            20                  25                  30

Gly Ser Phe Gly Ala Val Tyr Phe Ala Thr Asn Ala His Thr Ser Glu
        35                  40                  45

Val Val Ala Ile Lys Lys Met Ser Tyr Ser Gly Lys Gln Thr His Glu
    50                  55                  60

Lys Trp Gln Asp Ile Leu Lys Glu Val Lys Phe Leu Arg Gln Leu Lys
65                  70                  75                  80

His Pro Asn Thr Ile Glu Tyr Lys Gly Cys Tyr Leu Lys Glu His Thr
                85                  90                  95

Ala Trp Leu Val Met Glu Tyr Cys Leu Gly Ser Ala Ser Asp Leu Leu
            100                 105                 110

Glu Val His Lys Lys Pro Leu Gln Glu Val Glu Ile Ala Ala Ile Thr
        115                 120                 125

His Gly Ala Leu His Gly Leu Ala Tyr Leu His Ser His Ala Leu Ile
    130                 135                 140

His Arg Asp Ile Lys Ala Gly Asn Ile Leu Leu Thr Glu Pro Gly Gln
145                 150                 155                 160

Val Lys Leu Ala Asp Phe Gly Ser Ala Ser Met Ala Ser Pro Ala Asn
                165                 170                 175

Ser Phe Val Gly Thr Pro Tyr Trp Met Ala Pro Glu Val Ile Leu Ala
            180                 185                 190

Met Asp Glu Gly Gln Tyr Asp Gly Lys Val Asp Ile Trp Ser Leu Gly
        195                 200                 205

Ile Thr Cys Ile Glu Leu Ala Glu Arg Lys Pro Pro Leu Phe Asn Met
    210                 215                 220

Asn Ala Met Ser Ala Leu Tyr His Ile Ala Gln Asn Asp Ser Pro Thr
225                 230                 235                 240

Leu Gln Ser Asn Glu Trp Thr Asp Ser Phe Arg Arg Phe Val Asp Tyr
                245                 250                 255

Cys Leu Gln Lys Ile Pro Gln Glu Arg Pro Thr Ser Ala Glu Leu Leu
            260                 265                 270

Arg His Asp Phe Val Arg Arg Asp Arg Pro Leu Arg Val Leu Ile Asp
        275                 280                 285

Leu Ile Gln Arg Thr Lys Asp Ala Val Arg Glu Leu Asp Asn Leu Gln
    290                 295                 300

Tyr Arg Lys Met Lys Lys Ile Leu Phe Gln Glu Thr Arg Asn Gly Pro
305                 310                 315                 320

Leu Asn Glu Ser Gln Glu Asp Glu Asp Ser Glu His Gly Thr Ser
                325                 330                 335

Leu Asn Arg Glu Met Asp Ser Leu Gly Ser Asn His Ser Ile Pro Ser
            340                 345                 350

Met Ser Val Thr Trp Asn Gln Pro Gln Gly Asn Gly Gln Pro Gly
        355                 360                 365

Gln Gln Pro Phe His Ser Lys His Val Arg Val Met Met His Asp Asp
    370                 375                 380

Glu Ser Thr Ile Asn Ser Ser Ser Val Val His Lys Lys Asp His
385                 390                 395                 400

Val Phe Ile Arg Asp Glu Ala Gly His Gly Asp Pro Arg Pro Glu Pro
                405                 410                 415
```

-continued

Arg Pro Thr Gln Ser Val Gln Ser Gln Ala Leu His Tyr Arg Asn Arg
            420                 425                 430

Glu Arg Phe Ala Thr Ile Lys Ser Ala Ser Leu Val Thr Arg Gln Ile
            435                 440                 445

His Glu His Glu Gln Glu Asn Glu Leu Arg Glu Gln Met Ser Gly Tyr
            450                 455                 460

Lys Arg Met Arg Arg Gln His Gln Lys Gln Leu Ile Ala Leu Glu Asn
465                 470                 475                 480

Lys Leu Lys Ala Glu Met Asp Glu His Arg Leu Lys Leu Gln Lys Glu
                485                 490                 495

Val Glu Thr His Ala Asn Asn Ser Ser Ile Glu Leu Glu Lys Leu Ala
                500                 505                 510

Lys Lys Gln Val Ala Ile Ile Glu Lys Glu Ala Lys Val Ala Ala Ala
            515                 520                 525

Asp Glu Lys Lys Phe Gln Gln Ile Leu Ala Gln Gln Lys Lys Asp
            530                 535                 540

Leu Thr Thr Phe Leu Glu Ser Gln Lys Lys Gln Tyr Lys Ile Cys Lys
545                 550                 555                 560

Glu Lys Ile Lys Glu Glu Met Asn Glu Asp His Ser Thr Pro Lys Lys
                565                 570                 575

Glu Lys Gln Glu Arg Ile Ser Lys His Lys Glu Asn Leu Gln His Thr
            580                 585                 590

Gln Ala Glu Glu Glu Ala His Leu Leu Thr Gln Gln Arg Leu Tyr Tyr
            595                 600                 605

Asp Lys Asn Cys Arg Phe Phe Lys Arg Lys Ile Met Ile Lys Arg His
610                 615                 620

Glu Val Glu Gln Gln Asn Ile Arg Glu Glu Leu Asn Lys Lys Arg Thr
625                 630                 635                 640

Gln Lys Glu Met Glu His Ala Met Leu Ile Arg His Asp Glu Ser Thr
                645                 650                 655

Arg Glu Leu Glu Tyr Arg Gln Leu His Thr Leu Gln Lys Leu Arg Met
                660                 665                 670

Asp Leu Ile Arg Leu Gln His Gln Thr Glu Leu Glu Asn Gln Leu Glu
            675                 680                 685

Tyr Asn Lys Arg Arg Glu Arg Glu Leu His Arg Lys His Val Met Glu
            690                 695                 700

Leu Arg Gln Gln Pro Lys Asn Leu Lys Ala Met Glu Met Gln Ile Lys
705                 710                 715                 720

Lys Gln Phe Gln Asp Thr Cys Lys Val Gln Thr Lys Gln Tyr Lys Ala
                725                 730                 735

Leu Lys Asn His Gln Leu Glu Val Thr Pro Lys Asn Glu His Lys Thr
            740                 745                 750

Ile Leu Lys Thr Leu Lys Asp Glu Gln Thr Arg Lys Leu Ala Ile Leu
            755                 760                 765

Ala Glu Gln Tyr Glu Gln Ser Ile Asn Glu Met Met Ala Ser Gln Ala
            770                 775                 780

Leu Arg Leu Asp Glu Ala Gln Glu Ala Glu Cys Gln Ala Leu Arg Leu
785                 790                 795                 800

Gln Leu Gln Gln Glu Met Glu Leu Leu Asn Ala Tyr Gln Ser Lys Ile
            805                 810                 815

Lys Met Gln Thr Glu Ala Gln His Glu Arg Glu Leu Gln Lys Leu Glu
            820                 825                 830

Gln Arg Val Ser Leu Arg Arg Ala His Leu Glu Gln Lys Ile Glu Glu
            835                 840                 845

```
Glu Leu Ala Ala Leu Gln Lys Glu Arg Ser Glu Arg Ile Lys Asn Leu
    850                 855                 860

Leu Glu Arg Gln Glu Arg Glu Ile Glu Thr Phe Asp Met Glu Ser Leu
865                 870                 875                 880

Arg Met Gly Phe Gly Asn Leu Val Thr Leu Asp Phe Pro Lys Glu Asp
                885                 890                 895

Tyr Arg

<210> SEQ ID NO 18
<211> LENGTH: 1005
<212> TYPE: PRT
<213> ORGANISM: Homo sapiens

<400> SEQUENCE: 18

Leu Leu Ser Arg Met Pro Ser Thr Asn Arg Ala Gly Ser Leu Lys Asp
1               5                   10                  15

Pro Glu Ile Ala Glu Leu Phe Phe Lys Glu Asp Pro Gly Lys Leu Phe
            20                  25                  30

Thr Asp Leu Arg Glu Ile Gly His Gly Ser Phe Gly Ala Val Tyr Phe
        35                  40                  45

Ala Arg Asp Val Arg Thr Asn Glu Val Val Ala Ile Lys Lys Met Ser
    50                  55                  60

Tyr Ser Gly Lys Gln Ser Thr Glu Lys Trp Gln Asp Ile Ile Lys Glu
65                  70                  75                  80

Val Lys Phe Leu Gln Arg Ile Lys His Pro Asn Ser Ile Glu Tyr Lys
                85                  90                  95

Gly Cys Tyr Leu Arg Glu His Thr Ala Trp Leu Val Met Glu Tyr Cys
            100                 105                 110

Leu Gly Ser Ala Ser Asp Leu Leu Glu Val His Lys Lys Pro Leu Gln
        115                 120                 125

Glu Val Glu Ile Ala Ala Ile Thr His Gly Ala Leu Gln Gly Leu Ala
    130                 135                 140

Tyr Leu His Ser His Thr Met Ile His Arg Asp Ile Lys Ala Gly Asn
145                 150                 155                 160

Ile Leu Leu Thr Glu Pro Gly Gln Val Lys Leu Ala Asp Phe Gly Ser
                165                 170                 175

Ala Ser Met Ala Ser Pro Ala Asn Ser Phe Val Gly Thr Pro Tyr Trp
            180                 185                 190

Met Ala Pro Glu Val Ile Leu Ala Met Asp Glu Gly Gln Tyr Asp Gly
        195                 200                 205

Lys Val Asp Val Trp Ser Leu Gly Ile Thr Cys Ile Glu Leu Ala Glu
    210                 215                 220

Arg Lys Pro Pro Leu Phe Asn Met Asn Ala Met Ser Ala Leu Tyr His
225                 230                 235                 240

Ile Ala Gln Asn Glu Ser Pro Thr Leu Gln Ser Asn Glu Trp Ser Asp
                245                 250                 255

Tyr Phe Arg Asn Phe Val Asp Ser Cys Leu Gln Lys Ile Pro Gln Asp
            260                 265                 270

Arg Pro Thr Ser Glu Glu Leu Leu Lys His Ile Phe Val Leu Arg Glu
        275                 280                 285

Arg Pro Glu Thr Val Leu Ile Asp Leu Ile Gln Arg Thr Lys Asp Ala
    290                 295                 300

Val Arg Glu Leu Asp Asn Leu Gln Tyr Arg Lys Met Lys Lys Leu Leu
305                 310                 315                 320
```

-continued

```
Phe Gln Glu Ala His Asn Gly Pro Ala Val Glu Ala Gln Glu Glu
                325                 330                 335

Glu Glu Gln Asp His Gly Val Gly Arg Thr Gly Thr Val Asn Ser Val
            340                 345                 350

Gly Ser Asn Gln Ser Ile Pro Ser Met Ser Ile Ser Ala Ser Ser Gln
        355                 360                 365

Ser Ser Ser Val Asn Ser Leu Pro Asp Val Ser Asp Lys Ser Glu
    370                 375                 380

Leu Asp Met Met Glu Gly Asp His Thr Val Met Ser Asn Ser Ser Val
385                 390                 395                 400

Ile His Leu Lys Pro Glu Glu Asn Tyr Arg Glu Glu Gly Asp Pro
                405                 410                 415

Arg Thr Arg Ala Ser Asp Pro Gln Ser Pro Gln Val Ser Arg His
            420                 425                 430

Lys Ser His Tyr Arg Asn Arg Glu His Phe Ala Thr Ile Arg Thr Ala
        435                 440                 445

Ser Leu Val Thr Arg Gln Met Gln Glu His Glu Gln Asp Ser Glu Leu
    450                 455                 460

Arg Glu Gln Met Ser Gly Tyr Lys Arg Met Arg Arg Gln His Gln Lys
465                 470                 475                 480

Gln Leu Met Thr Leu Glu Asn Lys Leu Lys Ala Glu Met Asp Glu His
                485                 490                 495

Arg Leu Arg Leu Asp Lys Asp Leu Glu Thr Gln Arg Asn Asn Phe Ala
            500                 505                 510

Ala Glu Met Glu Lys Leu Ile Lys Lys His Gln Ala Ala Met Glu Lys
        515                 520                 525

Glu Ala Lys Val Met Ser Asn Glu Glu Lys Lys Phe Gln Gln His Ile
    530                 535                 540

Gln Ala Gln Gln Lys Lys Glu Leu Asn Ser Phe Leu Glu Ser Gln Lys
545                 550                 555                 560

Arg Glu Tyr Lys Leu Arg Lys Glu Gln Leu Lys Glu Glu Leu Asn Glu
                565                 570                 575

Asn Gln Ser Thr Pro Lys Lys Glu Lys Gln Glu Trp Leu Ser Lys Gln
            580                 585                 590

Lys Glu Asn Ile Gln His Phe Gln Ala Glu Glu Ala Asn Leu Leu
        595                 600                 605

Arg Arg Gln Arg Gln Tyr Leu Glu Leu Glu Cys Arg Arg Phe Lys Arg
    610                 615                 620

Arg Met Leu Leu Gly Arg His Asn Leu Glu Gln Asp Leu Val Arg Glu
625                 630                 635                 640

Glu Leu Asn Lys Arg Gln Thr Gln Lys Asp Leu Glu His Ala Met Leu
                645                 650                 655

Leu Arg Gln His Glu Ser Met Gln Glu Leu Glu Phe Arg His Leu Asn
            660                 665                 670

Thr Ile Gln Lys Met Arg Cys Glu Leu Ile Arg Leu Gln His Gln Thr
        675                 680                 685

Glu Leu Thr Asn Gln Leu Glu Tyr Asn Lys Arg Arg Glu Arg Glu Leu
    690                 695                 700

Arg Arg Lys His Val Met Glu Val Arg Gln Gln Pro Lys Ser Leu Lys
705                 710                 715                 720

Ser Lys Glu Leu Gln Ile Lys Lys Gln Phe Gln Asp Thr Cys Lys Ile
                725                 730                 735

Gln Thr Arg Gln Tyr Lys Ala Leu Arg Asn His Leu Leu Glu Thr Thr
            740                 745                 750
```

-continued

```
Pro Lys Ser Glu His Lys Ala Val Leu Lys Arg Leu Lys Glu Glu Gln
        755                 760                 765

Thr Arg Lys Leu Ala Ile Leu Ala Glu Gln Tyr Asp His Ser Ile Asn
        770                 775                 780

Glu Met Leu Ser Thr Gln Ala Leu Arg Leu Asp Glu Ala Gln Glu Ala
785                 790                 795                 800

Glu Cys Gln Val Leu Lys Met Gln Leu Gln Gln Glu Leu Glu Leu Leu
                805                 810                 815

Asn Ala Tyr Gln Ser Lys Ile Lys Met Gln Ala Glu Ala Gln His Asp
                820                 825                 830

Arg Glu Leu Arg Glu Leu Glu Gln Arg Val Ser Leu Arg Arg Ala Leu
                835                 840                 845

Leu Glu Gln Lys Ile Glu Glu Met Leu Ala Leu Gln Asn Glu Arg
        850                 855                 860

Thr Glu Arg Ile Arg Ser Leu Leu Glu Arg Gln Ala Arg Glu Ile Glu
865                 870                 875                 880

Ala Phe Asp Ser Glu Ser Met Arg Leu Gly Phe Ser Asn Met Val Leu
                885                 890                 895

Ser Asn Leu Ser Pro Glu Ala Phe Ser His Ser Tyr Pro Gly Ala Ser
                900                 905                 910

Gly Trp Ser His Asn Pro Thr Gly Gly Pro Gly Pro His Trp Gly His
        915                 920                 925

Pro Met Gly Gly Pro Pro Gln Ala Trp Gly His Pro Met Gln Gly Gly
        930                 935                 940

Pro Gln Pro Trp Gly His Pro Ser Gly Pro Met Gln Gly Val Pro Arg
945                 950                 955                 960

Gly Ser Ser Met Gly Val Arg Asn Ser Pro Gln Ala Leu Arg Arg Thr
                965                 970                 975

Ala Ser Gly Gly Arg Thr Glu Gln Gly Met Ser Arg Ser Thr Ser Val
                980                 985                 990

Thr Ser Gln Ile Ser Asn Gly Ser  His Met Ser Tyr Thr
        995                 1000                1005
```

TAOJIKS AS MODIFIERS OF THE BETA-CATENIN PATHWAY AND METHODS OF USE

REFERENCE TO RELATED APPLICATIONS

This application claims priority to U.S. provisional patent application No. 60/340,312 filed Dec. 13, 2001. The content of the prior application is hereby incorporated in its entirety.

BACKGROUND OF THE INVENTION

Beta-catenin is an adherens junction protein. Adherens junctions (AJs; also called the zonula adherens) are critical for the establishment and maintenance of epithelial layers, such as those lining organ surfaces. AJs mediate adhesion between cells, communicate a signal that neighboring cells are present, and anchor the actin cytoskeleton. In serving these roles, AJs regulate normal cell growth and behavior. At several stages of embryogenesis, wound healing, and tumor cell metastasis, cells form and leave epithelia. This process, which involves the disruption and reestablishment of epithelial cell-cell contacts, may be regulated by the disassembly and assembly of AJs. AJs may also function in the transmission of the 'contact inhibition' signal, which instructs cells to stop dividing once an epithelial sheet is complete.

The AJ is a multiprotein complex assembled around calcium-regulated cell adhesion molecules called cadherins (Peifer, M.(1993) Science 262: 1667-1668). Cadherins are transmembrane proteins: the extracellular domain mediates homotypic adhesion with cadherins on neighboring cells, and the intracellular domain interacts with cytoplasmic proteins that transmit the adhesion signal and anchor the AJ to the actin cytoskeleton. These cytoplasmic proteins include the alpha-, beta-, and gamma-catenins. The beta-catenin protein shares 70% amino acid identity with both plakoglobin, which is found in desmosomes (another type of intracellular junction), and the product of the Drosophila segment polarity gene 'armadillo'. Armadillo is part of a multiprotein AJ complex in Drosophila that also includes some homologs of alpha-catenin and cadherin, and genetic studies indicate that it is required for cell adhesion and cytoskeletal integrity.

Beta-catenin, in addition to its role as a cell adhesion component, also functions as a transcriptional co-activator in the Wnt signaling pathway through its interactions with the family of Tcf and Lef transcription factors (for a review see Polakis, (1999) Current Opinion in Genetics & Development, 9:15-21 and Gat U., et al., (1998) Cell 95:605-614).

The APC gene, which is mutant in adenomatous polyposis of the colon, is a negative regulator of beta-catenin signaling (Korinek, V. et al., (1997) Science 275: 1784-1787; Morin, P. J., et al., (1997) Science 275: 1787-1790). The APC protein normally binds to beta-catenin and, in combination with other proteins (including glycogen synthase kinase-3b and axin, is required for the efficient degradation of b-catenin. The regulation of beta-catenin is critical to the tumor suppressive effect of APC and that this regulation can be circumvented by mutations in either APC or beta-catenin.

While mammals contain only a single beta-catenin gene, C. elegans contains three (Korswagen H C, et al., (2000) Nature 406:527-32). Each worm beta-catenin appears to carry out unique functions (Korswagen H C, et al., (2000) Nature 406:527-32, Nartarajan L et al. (2001) Genetics 159: 159-72). Because of the divergence of function in C. elegans, it is possible to specifically study beta-catenin role in cell adhesion, which is mediated by the C. elegans beta-catenin HMP-2.

Eukaryotic cells respond to extracellular stimuli by recruiting signal transduction pathways, many of which employ protein Ser/Thr kinases of the ERK family (Levin, D. E., and Errede, B. (1995) Curr. Opin. Cell Biol. 7, 197-202). The ubiquity of ERKs and their upstream activators, the MEKs, in signal transduction was first appreciated from studies of yeast (Herskowitz, I. (1995) Cell 80, 187-197). Part of the cellular response to toxins, physical stresses and inflammatory cytokines occurs by signalling via the stress-activated protein kinase (SAPK) and p38 reactivating kinase pathways (Kyriakis, J. M., and Avruch, J. (1990) J. Biol. Chem. 265, 17355-17363; Kyriakis, J. M., et al., (1991) J. Biol. Chem. 266, 10043-10046; Pulverer, B. J., et al., (1991) Nature 353, 670-674). These stress-responsive kinase pathways are structurally similar, but functionally distinct, from the archetypal mitogen-activated protein kinases (MAPKs or ERKs). The stimuli that start the pathway result in modification of cellular gene expression, growth arrest, apoptosis, or activation of immune and reticuloendothelial cells. TAO1 (thousand and one amino acid) is a protein kinase that may play a role in regulating stress-responsive MAP kinase pathways (Hutchison, M., et al (1998). J Biol Chem 273:28625-32). KIAA1361 is a protein with strong similarity with TAO 1. JIK (JNK-SAPK inhibitory kinase) is an STE20-like serine/threonine kinase and member of the GCK-like subfamily of Ste20 kinases. JIK is activated by ligand-bound EGF receptors, inhibits the JNK/SAPK signaling pathway, and also interacts with IRE1 (a gene involved in endoplasmic reticulum stress response) (Tassi, E., et al (1999) J Biol Chem 274:33287-95; Zhang, W., et al (2000) Biochem Biophys Res Commun 274: 872-9; Yoneda, T., et al (2001) J Biol Chem 276:13935-40).

The ability to manipulate the genomes of model organisms such as C. elegans provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Dulubova I, et al, J Neurochem 2001 April; 77(1):229-38; Cai T, et al., Diabetologia 2001 January; 44(1):81-8; Pasquinelli A E, et al., Nature. Nov. 2, 2000; 408(6808):37-8; Ivanov I P, et al., EMBO J Apr. 17, 2000; 19(8):1907-17; Vajo Z et al., Mamm Genome 1999 October; 10(10): 1000-4). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as beta-catenin, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the beta-catenin pathway in C. elegans, and identified their human orthologs, hereinafter referred to as TAO and JIK related kinases (TAOJIK). The invention provides methods for utilizing these beta-catenin modifier genes and polypeptides to identify TAOJIK-modulating agents that are candidate therapeutic agents that can be used in the treatment of disorders associated with defective or impaired beta-catenin function and/or TAOJIK function. Preferred TAOJIK-modulating agents specifically bind to TAOJIK polypeptides and restore beta-catenin function. Other preferred TAOJIK-modulating agents are nucleic acid modulators such as antisense oligomers and RNAi that repress TAOJIK gene expression or product activity by, for example, binding to and inhibiting the respective nucleic acid (i.e. DNA or mRNA).

TAOJIK modulating agents may be evaluated by any convenient in vitro or in vivo assay for molecular interaction with a TAOJIK polypeptide or nucleic acid. In one embodiment, candidate TAOJIK modulating agents are tested with an assay system comprising a TAOJIK polypeptide or nucleic acid. Agents that produce a change in the activity of the assay system relative to controls are identified as candidate beta-catenin modulating agents. The assay system may be cell-based or cell-free. TAOJIK-modulating agents include TAOJIK related proteins (e.g. dominant negative mutants, and biotherapeutics); TAOJIK-specific antibodies; TAOJIK-specific antisense oligomers and other nucleic acid modulators; and chemical agents that specifically bind to or interact with TAOJIK or compete with TAOJIK binding partner (e.g. by binding to a TAOJIK binding partner). In one specific embodiment, a small molecule modulator is identified using a kinase assay. In specific embodiments, the screening assay system is selected from a binding assay, an apoptosis assay, a cell proliferation assay, an angiogenesis assay, and a hypoxic induction assay.

In another embodiment, candidate beta-catenin pathway modulating agents are further tested using a second assay system that detects changes in the beta-catenin pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the beta-catenin pathway, such as an angiogenic, apoptotic, or cell proliferation disorder (e.g. cancer).

The invention further provides methods for modulating the TAOJIK function and/or the beta-catenin pathway in a mammalian cell by contacting the mammalian cell with an agent that specifically binds a TAOJIK polypeptide or nucleic acid. The agent may be a small molecule modulator, a nucleic acid modulator, or an antibody and may be administered to a mammalian animal predetermined to have a pathology associated the beta-catenin pathway.

DETAILED DESCRIPTION OF THE INVENTION

Genetic screens were designed to identify modifiers of the beta-catenin pathway in *C. elegans*. A weak allele of beta-catenin was used in our screen (a homozygous viable mutant of beta-catenin, allele qm39). The hmp-2 (qm-39) strain produces larval worms with a highly penetrant lumpy body phenotype in first stage larval worms (L1s). Various specific genes were silenced by RNA inhibition (RNAi). Methods for using RNAi to silence genes in *C. elegans* are known in the art (Fire A, et al., 1998 Nature 391:806-811; Fire, A. Trends Genet. 15, 358-363 (1999); WO9932619). Genes causing altered phenotypes in the worms were identified as modifiers of the beta-catenin pathway. A modifier of particular interest was T17E9.1. Accordingly, vertebrate orthologs of these modifiers, and preferably the human orthologs, TAOJIK genes (i.e., nucleic acids and polypeptides) are attractive drug targets for the treatment of pathologies associated with a defective beta-catenin signaling pathway, such as cancer.

In vitro and in vivo methods of assessing TAOJIK function are provided herein. Modulation of the TAOJIK or their respective binding partners is useful for understanding the association of the beta-catenin pathway and its members in normal and disease conditions and for developing diagnostics and therapeutic modalities for beta-catenin related pathologies. TAOJIK-modulating agents that act by inhibiting or enhancing TAOJIK expression, directly or indirectly, for example, by affecting a TAOJIK function such as enzymatic (e.g., catalytic) or binding activity, can be identified using methods provided herein. TAOJIK modulating agents are useful in diagnosis, therapy and pharmaceutical development.

Nucleic Acids and Polypeptides of the Invention

Sequences related to TAOJIK nucleic acids and polypeptides that can be used in the invention are disclosed in Genbank (referenced by Genbank identifier (GI) number) as GI#s 4759207 (SEQ ID NO: 1), 15929548 (SEQ ID NO:2), 7706400 (SEQ ID NO:4), 7705559 (SEQ ID NO:5), 20552662 (SEQ ID NO:6), 12803830 (SEQ ID NO:7), 19923463 (SEQ ID NO:8), 15302531 (SEQ ID NO:9), 7243102 (SEQ ID NO:10), 18587661 (SEQ ID NO:11), 20559660 (SEQ ID NO:12), 11596143 (SEQ ID NO:13), and 12803830 (SEQ ID NO: 15) for nucleic acid, and GI#s 4759208 (SEQ ID NO: 16), 7705560 (SEQ ID NO: 17), and 7243103 (SEQ ID NO:18) for polypeptides. Additionally, nucleic acid sequences of SEQ ID NOs:3 and 14 can also be used in the invention.

TAOJIKs are kinase proteins with kinase domains. The term "TAOJIK polypeptide" refers to a full-length TAOJIK protein or a functionally active fragment or derivative thereof. A "functionally active" TAOJIK fragment or derivative exhibits one or more functional activities associated with a full-length, wild-type TAOJIK protein, such as antigenic or immunogenic activity, enzymatic activity, ability to bind natural cellular substrates, etc. The functional activity of TAOJIK proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active TAOJIK polypeptide is a TAOJIK derivative capable of rescuing defective endogenous TAOJIK activity, such as in cell based or animal assays; the rescuing derivative may be from the same or a different species. For purposes herein, functionally active fragments also include those fragments that comprise one or more structural domains of a TAOJIK, such as a kinase domain or a binding domain. Protein domains can be identified using the PFAM program (Bateman A., et al., Nucleic Acids Res, 1999, 27:260-2). For example, the kinase (PFAM 00069) domain of TAOJIK from GI#s 4759208, 7705560, and 7243103 (SEQ ID NOs:16, 17, and 18, respectively) are located at approximately amino acid residues 28 to 281, 24 to 277, and 32 to 285, respectively. Methods for obtaining TAOJIK polypeptides are also further described below. In some embodiments, preferred fragments are functionally active, domain-containing fragments comprising at least 25 contiguous amino acids, preferably at least 50, more preferably 75, and most preferably at least 100 contiguous amino acids of any one of SEQ ID NOs:16-18 (a TAOJIK). In further preferred embodiments, the fragment comprises the entire kinase (functionally active) domain.

The term "TAOJIK nucleic acid" refers to a DNA or RNA molecule that encodes a TAOJIK polypeptide. Preferably, the TAOJIK polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human TAOJIK. Methods of identifying orthlogs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *C. elegans*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein.; W.R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of any of SEQ ID NOs:1-15. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of any one of SEQ ID NOs:1-15 under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of TAOJIK Nucleic Acids and Polypeptides TAOJIK nucleic acids and polypeptides, useful for identifying and testing agents that modulate TAOJIK function and for other applications related to the involvement of TAOJIK in the beta-catenin pathway. TAOJIK nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a TAOJIK protein for assays used to assess TAOJIK function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant TAOJIK is expressed in a cell line known to have defective beta-catenin function. The recombinant cells are used in cell-based screening assay systems of the invention, as described further below.

The nucleotide sequence encoding a TAOJIK polypeptide can be inserted into any appropriate expression vector. The necessary transcriptional and translational signals, including promoter/enhancer element, can derive from the native TAOJIK gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the TAOJIK gene product, the expression vector can comprise a promoter operably linked to a TAOJIK gene nucleic acid, one or more origins of replication, and, one or more selectable markers (e.g. thymidine kinase activity, resistance to antibiotics, etc.). Alternatively, recombinant expression vectors can be identified by assaying for the expression of the TAOJIK gene product based on the physical or functional properties of the TAOJIK protein in in vitro assay systems (e.g. immunoassays).

The TAOJIK protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the TAOJIK gene sequence is identified, the gene product can be isolated and purified using standard methods (e.g. ion exchange, affinity, and gel exclusion chromatography; centrifugation; differential solubility; electrophoresis). Alternatively, native TAOJIK proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of TAOJIK or other genes associated with the beta-catenin pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter TAOJIK expression may be used in in vivo assays to test for activity of a candidate beta-catenin modulating agent, or to further assess the role of TAOJIK in a beta-catenin pathway process such as apoptosis or cell proliferation. Preferably, the altered TAOJIK expression results in a detectable phenotype, such as decreased or increased levels of cell proliferation, angiogenesis, or apoptosis compared to control animals having normal TAOJIK expression. The genetically modified animal may additionally have altered beta-catenin expression (e.g. beta-catenin knockout). Preferred genetically modified animals are mammals such as primates, rodents (preferably mice or rats), among others. Preferred non-mammalian species include zebrafish, C. elegans, and Drosophila. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic Drosophila see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000);136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous TAOJIK gene that results in a decrease of TAOJIK function, preferably such that TAOJIK expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse TAOJIK gene is used to construct a homologous recombination vector suitable for altering an endogenous TAOJIK gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the TAOJIK gene, e.g., by introduction of additional copies of TAOJIK, or by operatively inserting a regulatory sequence that provides for altered expression of an endogenous copy of the TAOJIK gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of *Saccharomyces cerevisiae* (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the beta-catenin pathway, as animal models of disease and disorders implicating defective beta-catenin function, and for in vivo testing of candidate therapeutic agents, such as those identified in screens described below. The candidate therapeutic agents are administered to a genetically modified animal having altered TAOJIK function and phenotypic changes are compared with appropriate control animals such as genetically modified animals that receive placebo treatment, and/or animals with unaltered TAOJIK expression that receive candidate therapeutic agent.

In addition to the above-described genetically modified animals having altered TAOJIK function, animal models having defective beta-catenin function (and otherwise normal TAOJIK function), can be used in the methods of the present invention. For example, a beta-catenin knockout mouse can be used to assess, in vivo, the activity of a candidate beta-catenin modulating agent identified in one of the in vitro assays described below. Preferably, the candidate beta-catenin modulating agent when administered to a model system with cells defective in beta-catenin function, produces a detectable phenotypic change in the model system indicating that the beta-catenin function is restored, i.e., the cells exhibit normal cell cycle progression.

Modulating Agents

The invention provides methods to identify agents that interact with and/or modulate the function of TAOJIK and/or the beta-catenin pathway. Modulating agents identified by the methods are also part of the invention. Such agents are useful in a variety of diagnostic and therapeutic applications associated with the beta-catenin pathway, as well as in further analysis of the TAOJIK protein and its contribution to the beta-catenin pathway. Accordingly, the invention also provides methods for modulating the beta-catenin pathway comprising the step of specifically modulating TAOJIK activity by administering a TAOJIK-interacting or -modulating agent.

As used herein, a "TAOJIK-modulating agent" is any agent that modulates TAOJIK function, for example, an agent that interacts with TAOJIK to inhibit or enhance TAOJIK activity or otherwise affect normal TAOJIK function. TAOJIK function can be affected at any level, including transcription, protein expression, protein localization, and cellular or extracellular activity. In a preferred embodiment, the TAOJIK-modulating agent specifically modulates the function of the TAOJIK. The phrases "specific modulating agent", "specifically modulates", etc., are used herein to refer to modulating agents that directly bind to the TAOJIK polypeptide or nucleic acid, and preferably inhibit, enhance, or otherwise alter, the function of the TAOJIK. These phrases also encompasses modulating agents that alter the interaction of the TAOJIK with a binding partner, substrate, or cofactor (e.g. by binding to a binding partner of a TAOJIK, or to a protein/binding partner complex, and altering TAOJIK function). In a further preferred embodiment, the TAOJIK-modulating agent is a modulator of the beta-catenin pathway (e.g. it restores and/or upregulates beta-catenin function) and thus is also a beta-catenin-modulating agent.

Preferred TAOJIK-modulating agents include small molecule compounds; TAOJIK-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., $19^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Synthetic compounds may be rationally designed or identified based on known or inferred properties of the TAOJIK protein or may be identified by screening compound libraries. Alternative appropriate modulators of this class are natural products, particularly secondary metabolites from organisms such as plants or fungi, which can also be identified by screening compound libraries for TAOJIK-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the beta-catenin pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific TAOJIK-interacting proteins are useful in a variety of diagnostic and therapeutic applications related to the beta-catenin pathway and related disorders, as well as in validation assays for other TAOJIK-modulating agents. In a preferred embodiment, TAOJIK-interacting proteins affect normal TAOJIK function, including transcription, protein expression, protein localization, and cellular or extra-cellular activity. In another embodiment, TAOJIK-interacting proteins are useful in detecting and providing information about the function of TAOJIK proteins, as is relevant to beta-catenin related disorders, such as cancer (e.g., for diagnostic means).

An TAOJIK-interacting protein may be endogenous, i.e. one that naturally interacts genetically or biochemically with a TAOJIK, such as a member of the TAOJIK pathway that modulates TAOJIK expression, localization, and/or activity. TAOJIK-modulators include dominant negative forms of TAOJIK-interacting proteins and of TAOJIK proteins themselves. Yeast two-hybrid and variant screens offer preferred methods for identifying endogenous TAOJIK-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes d (reviewed in, e.g., Pandley A and Mann M, Nature (2000) 405:837-846; Yates J R 3 Trends Genet (2000) 16:5-8).

An TAOJIK-interacting protein may be an exogenous protein, such as a TAOJIK-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). TAOJIK antibodies are further discussed below.

In preferred embodiments, a TAOJIK-interacting protein specifically binds a TAOJIK protein. In alternative preferred embodiments, a TAOJIK-modulating agent binds a TAOJIK substrate, binding partner, or cofactor.

Antibodies

In another embodiment, the protein modulator is a TAOJIK specific antibody agonist or antagonist. The antibodies have therapeutic and diagnostic utilities, and can be used in screening assays to identify TAOJIK modulators. The antibodies can also be used in dissecting the portions of the TAOJIK pathway responsible for various cellular responses and in the general processing and maturation of the TAOJIK.

Antibodies that specifically bind TAOJIK polypeptides can be generated using known methods. Preferably the antibody is specific to a mammalian ortholog of TAOJIK polypeptide, and more preferably, to human TAOJIK. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of TAOJIK which are particularly antigenic can be selected, for example, by routine screening of TAOJIK polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence shown in any of SEQ ID NOs:16-18. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of TAOJIK or substantially purified fragments thereof. If TAOJIK. fragments are used, they preferably comprise at least 10, and more preferably, at least 20 contiguous amino acids of a TAOJIK protein. In a particular embodiment, TAOJIK-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of TAOJIK-specific antibodies is assayed by an appropriate assay such as a solid phase enzyme-linked immunosorbant assay (ELISA) using immobilized corresponding TAOJIK polypeptides. Other assays, such as radioimmunoassays or fluorescent assays might also be used.

Chimeric antibodies specific to TAOJIK polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

TAOJIK-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859, 206; WO0073469).

Nucleic Acid Modulators

Other preferred TAOJIK-modulating agents comprise nucleic acid molecules, such as antisense oligomers or double stranded RNA (dsRNA), which generally inhibit TAOJIK activity. Preferred nucleic acid modulators interfere with the function of the TAOJIK nucleic acid such as DNA replication, transcription, translocation of the TAOJIK RNA to the site of protein translation, translation of protein from the TAOJIK RNA, splicing of the TAOJIK RNA to yield one or more mRNA species, or catalytic activity which may be engaged in or facilitated by the TAOJIK RNA.

In one embodiment, the antisense oligomer is an oligonucleotide that is sufficiently complementary to a TAOJIK mRNA to bind to and prevent translation, preferably by binding to the 5' untranslated region. TAOJIK-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/ 18193; Probst J C, Antisense Oligodeoxynucleotide and Ribozyme Design, Methods. (2000) 22(3):271-281; Summerton J, and Weller D. 1997 Antisense Nucleic Acid Drug Dev.:7:187-95; U.S. Pat. No. 5,235,033; and U.S. Pat. No. 5,378,841).

Alternative preferred TAOJIK nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a TAOJIK-specific nucleic acid modulator is used in an assay to further elucidate the role of the TAOJIK in the beta-catenin pathway, and/or its relationship to other members of the pathway. In another aspect of the invention, a TAOJIK-specific antisense oligomer is used as a therapeutic agent for treatment of beta-catenin-related disease states.

Assay Systems

The invention provides assay systems and screening methods for identifying specific modulators of TAOJIK activity. As used herein, an "assay system" encompasses all the components required for performing and analyzing results of an assay that detects and/or measures a particular event. In general, primary assays are used to identify or confirm a modulator's specific biochemical or molecular effect with respect to the TAOJIK nucleic acid or protein. In general, secondary assays further assess the activity of a TAOJIK modulating agent identified by a primary assay and may confirm that the modulating agent affects TAOJIK in a manner relevant to the beta-catenin pathway. In some cases, TAOJIK modulators will be directly tested in a secondary assay.

In a preferred embodiment, the screening method comprises contacting a suitable assay system comprising a TAOJIK polypeptide or nucleic acid with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates TAOJIK activity, and hence the beta-catenin pathway. The TAOJIK polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, calorimetric, spectrophotometric, and amperometric methods, to provide a read-out for the particular molecular event detected.

Cell-based screening assays usually require systems for recombinant expression of TAOJIK and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when TAOJIK-interacting proteins are used in screens to identify small molecule modulators, the binding specificity of the interacting protein to the TAOJIK protein may be assayed by various known methods such as substrate processing (e.g. ability of the candidate TAOJIK-specific binding agents to function as negative effectors in TAOJIK-expressing cells), binding equilibrium constants (usually at least about $10^7 \, M^{-1}$, preferably at least about $10^8 \, M^{-1}$, more preferably at least about $109 \, M^{-1}$), and immunogenicity (e.g. ability to elicit TAOJIK specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a TAOJIK polypeptide, a fusion protein thereof, or to cells or membranes bearing the polypeptide or fusion protein. The TAOJIK polypeptide can be full length or a fragment thereof that retains functional TAOJIK activity. The TAOJIK polypeptide may be fused to another polypeptide, such as a peptide tag for detection or anchoring, or to another tag. The TAOJIK polypeptide is preferably human TAOJIK, or is an ortholog or derivative thereof as described above. In a preferred embodiment, the screening assay detects candidate agent-based modulation of TAOJIK interaction with a binding target, such as an endogenous or exogenous protein or other substrate that has TAOJIK-specific binding activity, and can be used to assess normal TAOJIK gene function.

Suitable assay formats that may be adapted to screen for TAOJIK modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate TAOJIK and beta-catenin pathway modulators (e.g. U.S. Pat. No. 6,165,992 (kinase assays); U.S. Pat. Nos. 5,550,019 and 6,133,437 (apoptosis assays); U.S. Pat. Nos. 5,976,782, 6,225,118 and 6,444,434 (angiogenesis assays), among others). Specific preferred assays are described in more detail below.

Kinase assays. In some preferred embodiments the screening assay detects the ability of the test agent to modulate the kinase activity of a TAOJIK polypeptide. In further embodiments, a cell-free kinase assay system is used to identify a candidate beta-catenin modulating agent, and a secondary, cell-based assay, such as an apoptosis or hypoxic induction assay (described below), may be used to further characterize the candidate beta-catenin modulating agent. Many different assays for kinases have been reported in the literature and are well known to those skilled in the art (e.g. U.S. Pat. No. 6,165,992; Zhu et al., Nature Genetics (2000) 26:283-289; and WO0073469). Radioassays, which monitor the transfer of a gamma phosphate are frequently used. For instance, a scintillation assay for p56 (lck) kinase activity monitors the transfer of the gamma phosphate from gamma-$^{33}$P ATP to a biotinylated peptide substrate; the substrate is captured on a streptavidin coated bead that transmits the signal (Beveridge M et al., J Biomol Screen (2000) 5:205-212). This assay uses the scintillation proximity assay (SPA), in which only radioligand bound to receptors tethered to the surface of an SPA bead are detected by the scintillant immobilized within it, allowing binding to be measured without separation of bound from free ligand.

Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA (Sadick M D, Dev Biol Stand (1999) 97:121-133).

Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem Jul. 1, 1996; 238(2):159-64).

Apoptosis assays. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). An apoptosis assay system may comprise a cell that expresses a TAOJIK, and that optionally has defective beta-catenin function (e.g. beta-catenin is over-expressed or under-expressed relative to wild-type cells). A test agent can be added to the apoptosis assay system and changes in induction of apoptosis relative to controls where no test agent is added, identify candidate beta-catenin modulating agents. In some embodiments of the invention, an apoptosis assay may be used as a secondary assay to test a candidate beta-catenin modulating agents that is initially identified using a cell-free assay system. An apoptosis assay may also be used to test whether TAOJIK function plays a direct role in apoptosis. For example, an apoptosis assay may be performed on cells that over- or under-express TAOJIK relative to wild type cells. Differences in apoptotic response compared to wild type cells suggest that the TAOJIK plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman L S 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46).

Cell proliferation may also be assayed by colony formation in soft agar (Sambrook et al., Molecular Cloning, Cold Spring Harbor (1989)). For example, cells transformed with TAOJIK are seeded in soft agar plates, and colonies are measured and counted after two weeks incubation.

Involvement of a gene in the cell cycle may be assayed by flow cytometry (Gray J W et al. (1986) Int J Radiat Biol Relat Stud Phys Chem Med 49:237-55). Cells transfected with a TAOJIK may be stained with propidium iodide and evaluated in a flow cytometer (available from Becton Dickinson), which indicates accumulation of cells in different stages of the cell cycle.

Accordingly, a cell proliferation or cell cycle assay system may comprise a cell that expresses a TAOJIK, and that optionally has defective beta-catenin function (e.g. beta-catenin is over-expressed or under-expressed relative to wild-type cells). A test agent can be added to the assay system and changes in cell proliferation or cell cycle relative to controls where no test agent is added, identify candidate beta-catenin modulating agents. In some embodiments of the invention, the cell proliferation or cell cycle assay may be used as a secondary assay to test a candidate beta-catenin modulating agents that is initially identified using another assay system such as a cell-free kinase assay system. A cell proliferation assay may also be used to test whether TAOJIK function plays a direct role in cell proliferation or cell cycle. For example, a cell proliferation or cell cycle assay may be performed on cells that over- or under-express TAOJIK relative to wild type cells. Differences in proliferation or cell cycle compared to wild type cells suggest that the TAOJIK plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses a TAOJIK, and that optionally has defective beta-catenin function (e.g. beta-catenin is over-expressed or under-expressed relative to wild-type cells). A test agent can be added to the angiogenesis assay system and changes in angiogenesis relative to controls where no test agent is added, identify candidate beta-catenin modulating agents. In some embodiments of the invention, the angiogenesis assay may be used as a secondary assay to test a candidate beta-catenin modulating agents that is initially identified using another assay system. An angiogenesis assay may also be used to test whether TAOJIK function plays a direct role in cell proliferation. For example, an angiogenesis assay may be performed on cells that over- or under-express TAOJIK relative to wild type cells. Differences in angiogenesis compared to wild type cells suggests that the TAOJIK plays a direct role in angiogenesis. U.S. Pat. Nos. 5,976,782, 6,225,118 and 6,444,434, among others.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with TAOJIK in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses a TAOJIK, and that optionally has defective beta-catenin function (e.g. beta-catenin is over-expressed or under-expressed relative to wild-type cells). A test agent can be added to the hypoxic induction assay system and changes in hypoxic response relative to controls where no test agent is added, identify candidate beta-catenin modulating agents. In some embodiments of the invention, the hypoxic induction assay may be used as a secondary assay to test a candidate beta-catenin modulating agents that is initially identified using another assay system. A hypoxic induction assay may also be used to test whether TAOJIK function plays a direct role in the hypoxic response. For example, a hypoxic induction assay may be performed on cells that over- or under-express TAOJIK relative to wild type cells. Differences in hypoxic response compared to wild type cells suggests that the TAOJIK plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Tubulogenesis. Tubulogenesis assays monitor the ability of cultured cells, generally endothelial cells, to form tubular structures on a matrix substrate, which generally simulates the environment of the extracellular matrix. Exemplary substrates include Matrigel™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. Serum represents an undefined source of growth factors. In a preferred embodiment, the assay is performed with cells cultured in serum free medium, in order to control which process or pathway a candidate agent modulates. Moreover, we have found that different target genes respond differently to stimulation with different pro-angiogenic agents, including inflammatory angiogenic factors such as TNF-alpa. Thus, in a further preferred embodiment, a tubulogenesis assay system comprises testing a TAOJIK's response to a variety of factors, such as FGF, VEGF, phorbol myristate acetate (PMA), TNF-alpha, ephrin, etc.

Cell Migration. An invasion/migration assay (also called a migration assay) tests the ability of cells to overcome a physical barrier and to migrate towards pro-angiogenic signals. Migration assays are known in the art (e.g., Paik J H et al., 2001, J Biol Chem 276:11830-11837). In a typical experimental set-up, cultured endothelial cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific, South San Francisco, Calif.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. As described above, a preferred assay system for migration/invasion assays comprises testing a TAOJIK's response to a variety of pro-angiogenic factors, including tumor angiogenic and inflammatory angiogenic agents, and culturing the cells in serum free medium.

Sprouting assay. A sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143: 1341-52, 1998). Spheroids are harvested and seeded in 900 µl of methocel-collagen solution and pipetted into individual wells of a 24 well plate to allow collagen gel polymerization. Test agents are added after 30 min by pipetting 100 µl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

Primary Assays for Antibody Modulators

For antibody modulators, appropriate primary assays test is a binding assay that tests the antibody's affinity to and specificity for the TAOJIK protein. Methods for testing antibody affinity and specificity are well known in the art (Harlow and Lane, 1988, 1999, supra). The enzyme-linked immunosorbant assay (ELISA) is a preferred method for detecting TAOJIK-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance TAOJIK gene expression, preferably mRNA expression. In general, expression analysis comprises comparing TAOJIK expression in like populations of cells (e.g., two pools of cells that endogenously or recombinantly express TAOJIK) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that TAOJIK mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the TAOJIK protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve TAOJIK mRNA expression, may also be used to test nucleic acid modulators.

Secondary Assays

Secondary assays may be used to further assess the activity of TAOJIK-modulating agent identified by any of the above methods to confirm that the modulating agent affects TAOJIK in a manner relevant to the beta-catenin pathway. As used herein, TAOJIK-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with TAOJIK.

Secondary assays generally compare like populations of cells or animals (e.g., two pools of cells or animals that endogenously or recombinantly express TAOJIK) in the presence and absence of the candidate modulator. In general, such assays test whether treatment of cells or animals with a candidate TAOJIK-modulating agent results in changes in the beta-catenin pathway in comparison to untreated (or mock- or placebo-treated) cells or animals. Certain assays use "sensitized genetic backgrounds", which, as used herein, describe cells or animals engineered for altered expression of genes in the beta-catenin or interacting pathways.

Cell-Based Assays

Cell based assays may detect endogenous beta-catenin pathway activity or may rely on recombinant expression of beta-catenin pathway components. Any of the aforementioned assays may be used in this cell-based format. Candidate modulators are typically added to the cell media but may also be injected into cells or delivered by any other efficacious means.

Animal Assays

A variety of non-human animal models of normal or defective beta-catenin pathway may be used to test candidate TAOJIK modulators. Models for defective beta-catenin pathway typically use genetically modified animals that have been engineered to mis-express (e.g., over-express or lack expression in) genes involved in the beta-catenin pathway. Assays generally require systemic delivery of the candidate modulators, such as by oral administration, injection, etc.

In a preferred embodiment, beta-catenin pathway activity is assessed by monitoring neovascularization and angiogenesis. Animal models with defective and normal beta-catenin are used to test the candidate modulator's affect on TAOJIK in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the TAOJIK. The mixture is then injected subcutaneously (SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on TAOJIK is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the TAOJIK endogenously are injected in the flank, $1 \times 10^5$ to $1 \times 10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4°

C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific TAOJIK-modulating agents are useful in a variety of diagnostic and therapeutic applications where disease or disease prognosis is related to defects in the beta-catenin pathway, such as angiogenic, apoptotic, or cell proliferation disorders. Accordingly, the invention also provides methods for modulating the beta-catenin pathway in a cell, preferably a cell pre-determined to have defective or impaired beta-catenin function (e.g. due to overexpression, underexpression, or misexpression of beta-catenin, or due to gene mutations), comprising the step of administering an agent to the cell that specifically modulates TAOJIK activity. Preferably, the modulating agent produces a detectable phenotypic change in the cell indicating that the beta-catenin function is restored. The phrase "function is restored", and equivalents, as used herein, means that the desired phenotype is achieved, or is brought closer to normal compared to untreated cells. For example, with restored beta-catenin function, cell proliferation and/or progression through cell cycle may normalize, or be brought closer to normal relative to untreated cells. The invention also provides methods for treating disorders or disease associated with impaired beta-catenin function by administering a therapeutically effective amount of a TAOJIK-modulating agent that modulates the beta-catenin pathway. The invention further provides methods for modulating TAOJIK function in a cell, preferably a cell pre-determined to have defective or impaired TAOJIK function, by administering a TAOJIK-modulating agent. Additionally, the invention provides a method for treating disorders or disease associated with impaired TAOJIK function by administering a therapeutically effective amount of a TAOJIK-modulating agent.

The discovery that TAOJIK is implicated in beta-catenin pathway provides for a variety of methods that can be employed for the diagnostic and prognostic evaluation of diseases and disorders involving defects in the beta-catenin pathway and for the identification of subjects having a predisposition to such diseases and disorders.

Various expression analysis methods can be used to diagnose whether TAOJIK expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective beta-catenin signaling that express a TAOJIK, are identified as amenable to treatment with a TAOJIK modulating agent. In a preferred application, the beta-catenin defective tissue overexpresses a TAOJIK relative to normal tissue. For example, a Northern blot analysis of mRNA from tumor and normal cell lines, or from tumor and matching normal tissue samples from the same patient, using full or partial TAOJIK cDNA sequences as probes, can determine whether particular tumors express or overexpress TAOJIK. Alternatively, the TaqMan® is used for quantitative RT-PCR analysis of TAOJIK expression in cell lines, normal tissues and tumor samples (PE Applied Biosystems).

Various other diagnostic methods may be performed, for example, utilizing reagents such as the TAOJIK oligonucleotides, and antibodies directed against a TAOJIK, as described above for: (1) the detection of the presence of TAOJIK gene mutations, or the detection of either over- or under-expression of TAOJIK mRNA relative to the non-disorder state; (2) the detection of either an over- or an under-abundance of TAOJIK gene product relative to the non-disorder state; and (3) the detection of perturbations or abnormalities in the signal transduction pathway mediated by TAOJIK.

Thus, in a specific embodiment, the invention is drawn to a method for diagnosing a disease or disorder in a patient that is associated with alterations in TAOJIK expression, the method comprising: a) obtaining a biological sample from the patient; b) contacting the sample with a probe for TAOJIK expression; c) comparing results from step (b) with a control; and d) determining whether step (c) indicates a likelihood of the disease or disorder. Preferably, the disease is cancer, most preferably a cancer as shown in TABLE 2, or indicated as a result of immunohistochemistry analysis (Example VII). The probe may be either DNA or protein, including an antibody.

EXAMPLES

The following experimental section and examples are offered by way of illustration and not by way of limitation.

I. C. elegans Beta-Catenin Screen

The identification of mutants that suppress the cell adhesion defect of beta-catenin may lead to unique therapeutic targets that inhibit cell migration or metastasis. hmp-2 was initially identified in an EMS screen for defects in body elongation during embryonic morphogenesis (see Costa et al., (1998) The Journal of Cell Biology 1998, 141: 297-308). The loss of function allele hmp-2 (zu364) exhibits 99% embryonic lethality, with mutant embryos arresting during elongation and abnormal bulges forming on the dorsal side. About 1% of these embryos hatch to form viable lumpy larvae. The reduction of function allele hmp-2 (qm39) yields viable larvae with a characteristic lumpy appearance. When grown at 15° C., approximately 92% (SD 3.9) of the L1 larvae show this lumpy phenotype, with the penetrance of the phenotype decreasing as the animals molt and move through successive larval stages. For this screen, hmp-2 (qm39) worms were soaked at 15° C. in double stranded RNA (dsRNA) at the LA larval stage and the progeny were scored as L1 larvae for modification of the adhesion defect. The screen protocol is described below.

1) hmp-2 (qm39) animals were bleached and hatched on peptone free agarose plates to produce a synchronous population. Starved L1s were transferred to 10× peptone plates seeded with 750 µl OP50 (25% w/v in TB) and allowed to develop to the L4 larval stage.
2) dsRNA was dispensed in 6 µl aliquots into 96 well round bottom plates (Nunc #262162). LA animals were collected by suspension in M9 buffer, washed 2× with M9 to remove any excess OP50, and dispensed in 2 µl aliquots into the RNA to a total worm density of 75-100 worms per well. As a control, multiple wells contained only RNA resuspension buffer (1×IM buffer).
3) Animals were soaked in dsRNA at 15° C. for 24 hours.
4) Following dsRNA soaking, the animals were fed in the wells by addition of 25 µl liquid NGM+3% OP50. The animals were kept at 15° C. and allowed to become gravid and lay progeny in the wells, which took approximately 72 hours. Food levels were monitored visually during maturation and more was added as needed.
5) Following maturation, animals from each well were plated onto individual 6 cm peptone free agarose plates and placed at 15° C. overnight.
6) Animals on each plate were scored visually under the dissecting microscope for modification of the lumpy phenotype. Scoring was performed qualitatively, with an increase in dead embryos scored as enhancement and an increase in wild type appearing animals scored as suppression of the defect.
7) Retests of interesting suppressor candidates followed the same protocol as the primary screen with certain modifications: several retests were performed for each suppressor, retested candidates were encoded so that they could be scored blindly, and retested candidates were scored quantitatively. Each plate was scored by counting 100 total objects. An object was defined as either an embryo or an L1 stage larva. Each object was scored as one of the following: a wildtype appearing animal, a lumpy appearing animal, or an unhatched embryo. Scores were represented as the percentage of wildtype appearing animals relative to all objects scored. Wildtype animals were defined as L1 larvae with smooth cuticles that did not have any sort of lumpy body morphology.
8) A confirmed suppressor was one that was ≧2 standard deviations away from the mean of the controls for at least 3 of the four retest experiments.

BLAST analysis (Altschul et al., supra) was employed to identify orthologs of the C. elegans modifiers. For example, representative sequences from TAOJIK, GI#4759208 (SEQ ID NO: 16), GI#7705560 (SEQ ID NO:17) and GI#7243103 (SEQ ID NO:18) share 37%, 38%, and 38% amino acid identity, respectively, with the C. elegans T17E9.1.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. Jan. 1, 1999; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and dust (Remm M, and Sonnhammer E. Classification of transmembrane protein families in the *Caenorhabditis elegans* genome and identification of human orthologs. Genome Res. 2000 November; 10(11): 1679-89) programs. For example, the kinase (PFAM 00069) domain of TAOJIK from GI#s 4759208, 7705560, and 7243103 (SEQ ID NOs:16, 17, and 18, respectively) are located at approximately amino acid residues 28 to 281, 24 to 277, and 32 to 285, respectively.

Results:

Numbers shown in Table 1 are the percentage of wild type appearing animals relative to all animals (wtild-type, lumpy and embryos) scored per experiment. Control replicates were performed for each retest (#1-4) and the standard deviation for each control is listed beneath the average.

TABLE 1

| Gene ID | Retest #1 | Retest #2 | Retest #3 | Retest #4 | Mean | Deviation |
|---|---|---|---|---|---|---|
| T17E9.1 (kin-18) | 29 | 23 | 36 | 10 | 24.5 | 11.0302614 |
| Controls average | 9.4 | 9.4 | 8.1 | 8.1 | | |
| Deviation | 3.5 | 4.1 | 3.9 | 3.9 | | |

II. RNAi of C. elegans T17E9.1

T17E9.1/kin-18 (the C. elegans ortholog of human kinases TAO1, JIK, and KIAA1361) was initially identified in an RNAi gene inactivation screen as suppressors of a beta-catenin (hmp-2) lumpy body mutant phenotype resulting from reduced beta-catenin function in cytoskeletal organization at cell-cell adhesive junctions (Example I). Subsequent testing demonstrated that RNAi inactivation of the C. elegans gene also partially suppressed an axin (pry-1) developmental arrest mutant phenotype that appears to result from increased beta-catenin (bar-1) and TCF (pop-1) transcriptional activation function.

III. High-Throughput In Vitro Fluorescence Polarization Assay

Fluorescently-labeled TAOJIK peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of TAOJIK activity.

IV. High-Throughput In Vitro Binding Assay.

$^{33}$P-labeled TAOJIK peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate beta-catenin modulating agents.

V. Immunoprecipitations and Immunoblotting

For coprecipitation of transfected proteins, $3 \times 10^6$ appropriate recombinant cells containing the TAOJIK proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

VI. Kinase Assay

A purified or partially purified TAOJIK is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 µg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 µl. The reaction is initiated by the addition of $^{33}$P-gamma-ATP (0.5 µCi/ml) and incubated for 0.5 to 3 hours at room temperature. Negative controls are provided by the addition of EDTA, which chelates the divalent cation ($Mg^{2+}$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

VII. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, UC Davis, Clontech, Stratagene, Ardais, Genome Collaborative, and Ambion.

TAQMAN ANALYSIS. TaqMan analysis was used to assess expression levels of the disclosed genes in various samples.

RNA was extracted from each tissue sample using Qiagen (Valencia, Calif.) RNeasy kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of Applied Biosystems (Foster City, Calif.).

Primers for expression analysis using TaqMan assay (Applied Biosystems, Foster City, Calif.) were prepared according to the TaqMan protocols, and the following criteria: a) primer pairs were designed to span introns to eliminate genomic contamination, and b) each primer pair produced only one product. Expression analysis was performed using a 7900HT instrument.

Taqman reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples)>2× STDEV(all normal samples)).

Results are shown in Table 2. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 2

| GI# | SEQ ID NO | Breast | # of Pairs | Colon | # of Pairs | Head and Neck | # of Pairs | Kidney | # of Pairs | Lung | # of Pairs | Ovary | # of Pairs | Uterus | # of Pairs | Prostate | # of Pairs | Skin | # of Pairs |
|---|---|---|---|---|---|---|---|---|---|---|---|---|---|---|---|---|---|---|---|
| 4759207 | 1 | 0% | 19 | 12% | 33 | 0% | 8 | 21% | 24 | 0% | 21 | 8% | 12 | 5% | 19 | 8% | 12 | 33% | 3 |
| 7705559 | 5 | 5% | 19 | 15% | 33 | 13% | 8 | 21% | 24 | 5% | 20 | 8% | 12 | 5% | 19 | 25% | 12 | 0% | 3 |
| 7243102 | 10 | 5% | 19 | 12% | 33 | 13% | 8 | 4% | 24 | 5% | 20 | 9% | 12 | 16% | 19 | 17% | 12 | 33% | 3 |

IMMUNOHISTOCHEMICAL ANALYSIS. Immunohistochemistry was used to localize TAOJIK protein in human tissue sections according to known methods (Thomas Boenisch, ed. (2001) Handbook, Immunochemical Staining Methods, 3"I Edition, Dako Corporation, Carpinteria, CA). Antibody to TAOJIK GI#7243103 (SEQ ID NO:18) (mouse anti-TA01 antibody, BD Biosciences; San Diego, Calif.) was used for immunohistochemistry against tissue arrays containing 20 normal and 19 tumor tissues. Tissue sections were pre-treated with heat antigen retrieval in citrate buffer and the antibody was used at 20 ug/ml. In normal tissues, expression was observed in smooth muscle, breast myoepithelial cells and kidney glomeruli. In tumor tissues, there was overexpression in stomach stromal sarcomas, breast, endometrial, and bladder cancers.

VIII. TAOJIK RNAi

RNA interference experiments were carried out to knock down expression of TAOJIKs using small interfering RNAs (siRNA, Elbashir et al, supra). These experiments were performed against TAOJIKs GI#s 4759207 (SEQ ID NO: 1), 7705559 (SEQ ID NO:5), and 20559660 (SEQ ID NO: 12). For each experiment, three different siRNAs (21mer, double stranded RNA oligos with 2 base 3' overhangs, obtained from Genset Oligos/Proligo France SAS, France; Dharmacon Research Inc., Lafayette, Colo.) were transfected into cell lines (available from American Type Culture Collection (ATCC), Manassas, Va.) at 100 nM using oligofectamine (Invitrogen). A mock transfection reagent without siRNA was included with each experiment. Cells were incubated for 3 days at 37 degrees. At the end of each experiment, some wells of cells were harvested for protein extracts and used in western analysis and parallel cells were put through a BrdU ELISA to measure cell proliferation.

A. Effect of siRNA treatment of TAOJIKs in cells on beta-catenin. A549 lung cancer cells were grown in a 16 well slide (Nalge Nunc International; Rochester, N.Y.). Cells were fixed with 4% paraformaldehyde and labeled with B-catenin antibody (Cell Signaling), and rhodamine-conjugated phalloidin (Cytoskeleton Inc.; Denver, Colo.) for actin staining.

Results:

B-catenin localization to the plasma membrane was decreased in cells transfected with siRNAi against all TAOJIKs. In addition, no changes in cell-cell interactions were observed.

B. Effect of siRNA treatment of TAOJIKs on cell proliferation in cancer cell lines. Cell lines A549 (lung cancer line), MDA-MB-231T (breast cancer line), SW480, SW620, HCT116 (colon cancer cell lines) were incubated for 3 days with 100 nM duplex siRNA oligonucleotides, as described above. siRNA to luciferase and cyclin D1 were used as negative and positive controls, respectively. Cells in triplicate were incubated with 10% alamarBlue reagent (Biosource International; Camarillo, Calif.) according to standard protocol, to measure metabolism. Cells in triplicate were incubated with BrdU labeling reagent (Roche; Mannheim, Germany) according to standard protocol, to measure DNA synthesis in S phase cells.

Results:

A549 and MDA-MB-231T cells treated with siRNA against SEQ ID NOs:1, 5, and 12 showed approximately a 50% reduction in alamarBlue or BrdU values compared to mock transfection. Furthermore, SW480, SW620 and HCT116 cells treated with siRNA against SEQ ID NO: 12 showed approximately 50% decrease in Alamar blue or BrdU values compared to mock transfection. Thus, siRNA treatment of TAOJIKs reduces cell proliferation in cancer cell lines.

C. Western blot analysis of effect of siRNA treatment of TAOJIKs on beta-catenin, actin, and E-cadherin expression in A549, SW620, and HCT116 cancer cell lines. Triplicate wells from the above experiments A and B were lysed in RIPA buffer (Boston BioProducts, Inc.; Ashland, MA) with protease inhibitors (Roche) and phosphatase inhibitors. Protein concentrations of cell lysatcs were determined by the BCA method (Pierce; Rockford, Ill.). Samples were run on a 4-12% gradient gel (Invitrogen; Carlsbad, Calif.), transferred to PVDF membrane (Bedford, Mass.), and probed with antibodies against SEQ ID NO:18 (mouse anti-TA01 antibody, BD Biosciences; San Diego, Calif.); B-catenin (Cell Signaling Technology; Beverly, Mass.); actin (Accurate Chemical and Scientific Corporation; Westbury, NY); glyceraldehyde-3-phosphate dehydrogenase (Advanced Immuno Chemical, Inc.; Long Beach, CA); and E-cadherin (BD Biosciences).

Results:

In A549 cells, siRNA treatment of TAOJIKs SEQ ID NO: 1 and SEQ ID NO:5 decreased beta-catenin, E-cadherin and actin expression in A549 cells. KIAA1361 siRNA treatment of TAOJIK SEQ ID NO: 12 decreased expression of SEQ ID NO: 12 and E-cadherin.

CONCLUSION

Taken together, the RNAi and western blot experiments, in addition to reducing cell proliferation, suggest a link between TAOJIKs and beta-catenin function. Since the *C. elegans* T17E9.1 is also implicated in the beta catenin pathway, the link between TAOJIKs and the beta-catenin pathway provides compelling evidence of evolutionary functional conservation between these orthologs.

What is claimed is:

1. A method of identifying a candidate beta-catenin pathway modulating agent, said method comprising the steps of:
   (a) providing an in vitro cell-based assay system capable of detecting TAOJIK expression comprising mammalian cells in culture that express an endogenous and/or recombinant TAOJIK polypeptide comprising the amino acid sequence of SEQ ID NO:16, SEQ ID NO:17, or SEQ ID NO:18, wherein the cultured mammalian cells are living;
   (b) contacting the assay system with a candidate test agent; and
   (c) determining the expression of the TAOJIK in the assay system, wherein a change in TAOJIK expression between the presence and absence of said candidate test agent indicates that the candidate test agent is a candidate beta-catenin pathway modulating agent.

2. The method of claim 1, wherein the cultured cells additionally have defective beta-catenin function.

3. The method of claim 1, wherein the expression of TAOJIK is determined in the assay system using a binding assay comprising a TAOJIK polypeptide and wherein the candidate test agent is an anti-TAOJIK antibody.

4. The method of claim 1, wherein the expression of TAOJIK is determined in the assay system and wherein the candidate test agent is an organic non-peptide small molecule modulator having a molecular weight of less than 10,000 D.

* * * * *